United States Patent [19]
Frederickson et al.

[11] Patent Number: 6,005,399
[45] Date of Patent: Dec. 21, 1999

[54] SOLDER PASTE AND RESIDUE MEASUREMENT SYSTEM

[75] Inventors: Michael D. Frederickson, Indianapolis, Ind.; Martin A. Seitz, Brookfield, Wis.; Richard W. Hirthe; Mohammad N. Amin, both of Milwaukee, Wis.; Anthony L. Delieto, Camby, Ind.; Alex E. Cragoe, Indianapolis, Ind.; Jeff K. Latham, New Castle, Ind.; Patrick D. Riggs, Greenwood, Ind.

[73] Assignee: The United States of America as represented by the Secretary of the Navy, Washington, D.C.

[21] Appl. No.: 08/874,056

[22] Filed: Jun. 12, 1997

Related U.S. Application Data

[62] Division of application No. 08/393,765, Feb. 24, 1995, Pat. No. 5,656,933.

[51] Int. Cl.[6] .................................................. G01R 27/08
[52] U.S. Cl. .......................................... 324/693; 324/717
[58] Field of Search .................................... 324/71.2, 425, 324/691, 693, 700, 715, 717, 722, 724; 228/103, 104; 364/477.06

[56] References Cited

U.S. PATENT DOCUMENTS

| | | | |
|---|---|---|---|
| 5,369,370 | 11/1994 | Stratmann et al. | 324/693 |
| 5,448,178 | 9/1995 | Chen et al. | 324/700 |
| 5,485,392 | 1/1996 | Frederickson et al. | 364/477.06 |
| 5,674,375 | 10/1997 | Thompson | 324/700 |

*Primary Examiner*—Ernest Karlsen
*Attorney, Agent, or Firm*—Ron Billi

[57] ABSTRACT

This invention relates to an on-line statistical process control device for solder paste and residues. The invention consists of electronics hardware, software, and probing systems. The electrical hardware of the invention provides voltage and current measurements of solder paste materials, the software of the invention controls the hardware, provides real-time complex, non-linear least squares curve fitting for equivalent circuit analysis, data storage and retrieval of circuit parameters and behavior, and to statistical process control tracking and charting. The probing systems of the invention allows for 2, 3, and 4 probe surface and bulk measurements of the solder paste and residues.

1 Claim, 27 Drawing Sheets

TIME OF DAY

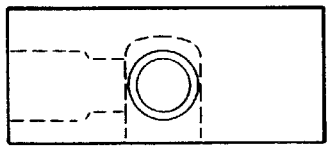
FIG. 23D
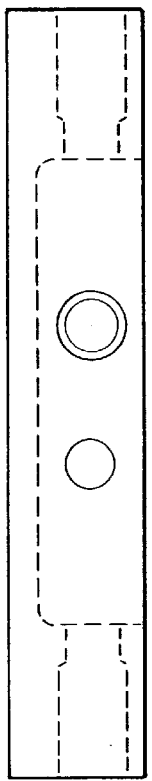
FIG. 23A
FIG. 23C
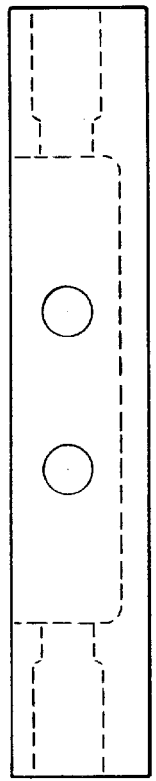
FIG. 23E
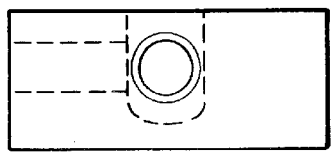
FIG. 23B

SOLDER PASTE AND RESIDUE MEASUREMENT SYSTEM

This a divisional of application Ser. No. 08/393,765 filed on Feb. 24, 1995, now U.S. Pat. No. 5,656,933.

The invention described herein may be manufactured and used by or for the Government of the United States of America for governmental purposes without payment of any royalties thereon or therefor.

FIELD OF THE INVENTION

This invention relates to an on-line statistical process control device for solder paste and residues. The invention consists of electronics hardware, software, and probing systems. The electrical hardware of the invention provides voltage and current measurements of solder paste materials, the software of the invention controls the hardware, provides real-time complex, non-linear least squares curve fitting for equivalent circuit analysis, data storage and retrieval of circuit parameters and behavior, and statistical process control tracking and charting. The probing systems of the invention allows for 2, 3, and 4 probe surface and bulk measurements of the solder paste and associated residues in manufacturing.

BACKGROUND OF THE INVENTION

A need for real-time solder paste process control is critical due to the dynamic nature of solder paste. Both the rheology and the solderability of solder paste can change drastically during manufacturing. These dynamic changes are dependent on the manufacturing environment and on the characteristics of the specific paste being used. An environment with high humidity can cause an increase in slump and, potentially, an increase in the probability of solder balls due to absorbed moisture. In addition, solder paste, over time, can either increase or decrease in viscosity; this classifies the paste as being thixotropic or rheopectic, respectively. The dynamic change in rheology can cause significant problems in the printability and slump of the solder paste. Lastly, any changes in the flux material can effect the solderability of the solder powder and can also have an impact of the rheologic nature of the paste due to the excessive build-up of reaction products between the flux activators and the metal oxides (such as $S_nO$ and/or $S_nO_2$).

Current methods of measuring the rheologic characteristics of solder paste entail the use of a viscometer. A viscometer is capable of measuring the viscosity of a solder paste material at a different shearing rates. Thus, the viscosity of a solder paste can be tracked at a reference shear rate and the thixotropic character of the solder paste can be tracked by calculating the change in viscosity over a change in shearing rate. Currently, there are two viscometers commonly used in the industry: a Malcolm Viscometer and a Brookfield Viscometer. Both of these systems allow a manufacturer to quantify both viscosity and thixotropic behavior.

The Brookfield viscometer uses a T-type spindle that rotates at a given rate in rotation and z-height while the Malcolm uses a screw-type spindle that causes the solder paste to pump up through the spindle to make a torque/viscosity measurement. The advantage of the Brookfield is in its acceptance by the industry and its maturity in quantifying viscosity. Due to the lack of controlled shearing with the T-type spindle, the Brookfield has limitations in measuring thixotropic behavior. The Malcolm is a relatively new viscometer design that was centered around the needs of solder paste rheologic measurements. The Malcolm is well designed to handle both viscosity and thixotropic measurements but does not have the same acceptance as the Brookfield in the electronics manufacturing industry. In both cases, neither system is capable of measuring the rheologic properties of solder paste once placed in a manufacturing environment. These systems are principally designed to make bulk rheologic measurements as an incoming inspection tool and typically require a significant amount of paste for an accurate measurement.

There are no other known electrical systems that measure and control solder paste materials currently available to the industry. Related U.S. Patents include U.S. Pat. No. 5,103,181 issued Apr. 7, 1992 to Gaisford et al. which is a composition and monitoring process that uses impedance measurements. In U.S. Pat. No. 4,939,469 a method for the evaluation of printed circuit boards is disclosed that uses the impedance spectra of the board to evaluate a number of characteristics such as moisture content. And U.S. Pat. Nos. 3,482,161, 3,440,529, and 3,448,380 all use spectroscopic analysis for sample analysis.

BRIEF DESCRIPTION OF THE DRAWINGS

The invention is described in more detail, by way of example only, with reference to the following drawings. Additional features necessary to the invention will be evident from the drawings.

FIG. 23A–D shows other views of the ¾-pole bulk probe of FIG. 22.

DETAILED DESCRIPTION OF THE PREFERRED EMBODIMENTS

Figure 1:
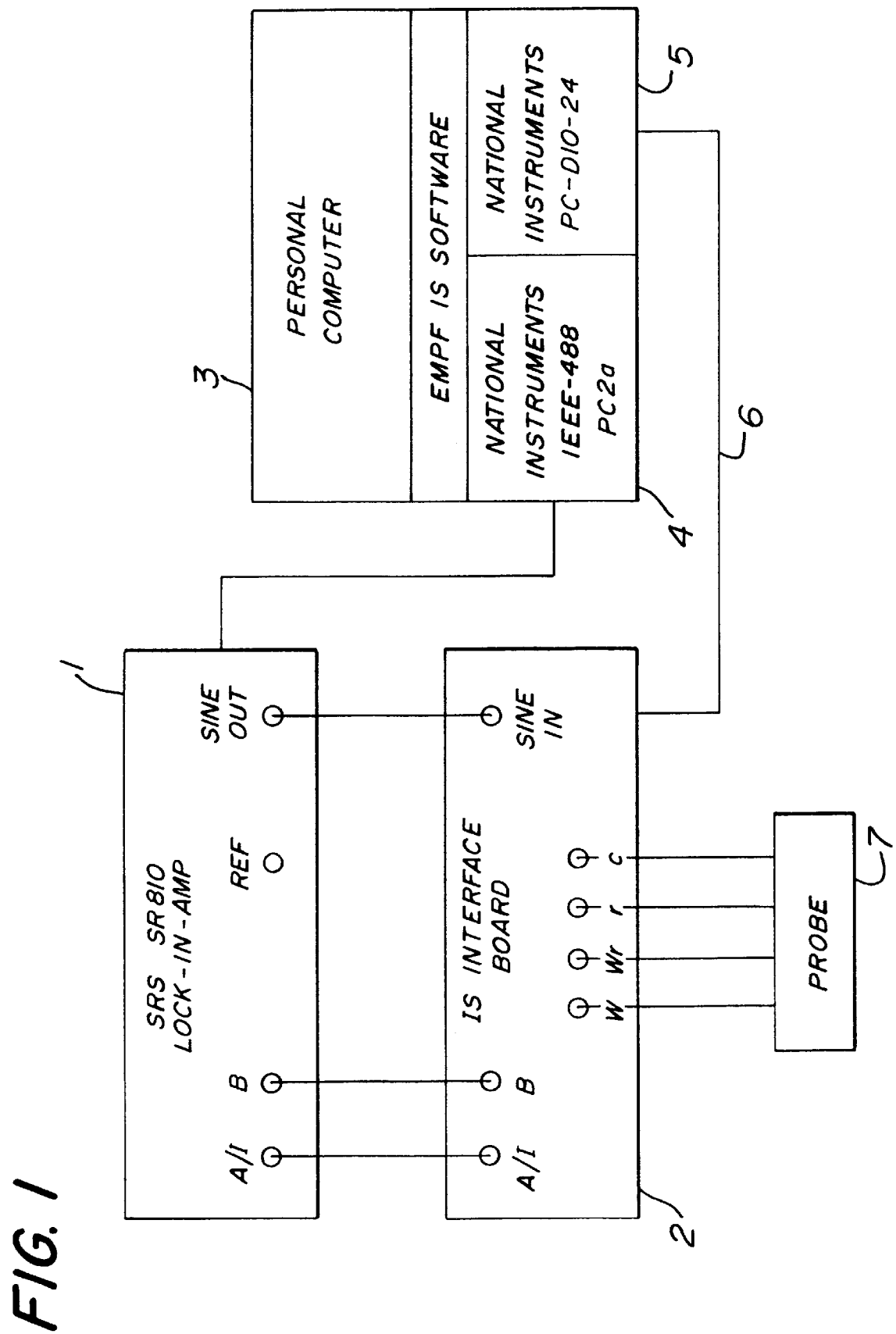
FIG. 1 is a block Diagram of the Instrumentation System
Figure 2:
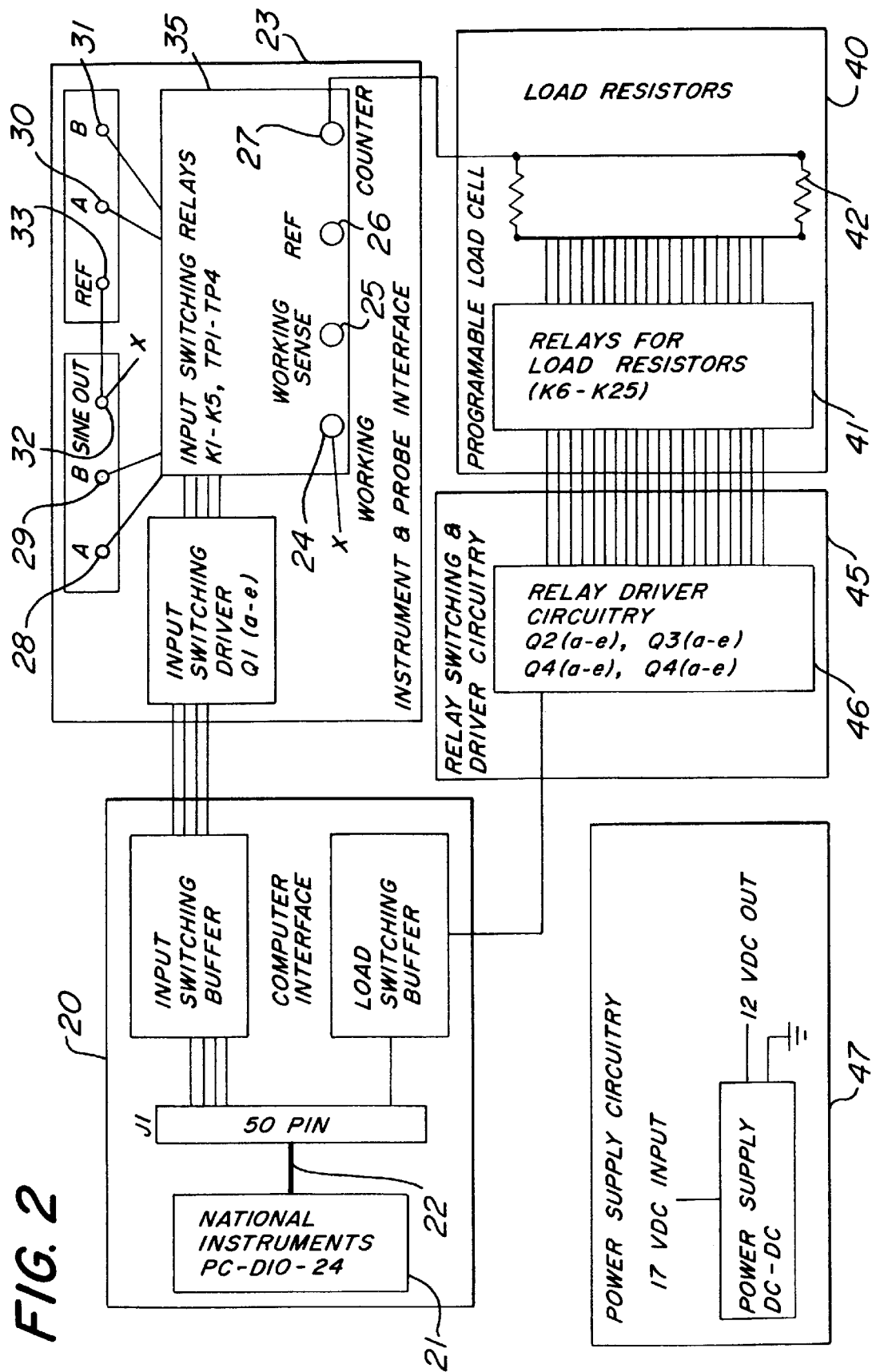
FIG. 2 is the Solder Paste Process Control Interface Board

The Solder Paste Process Control System is functionally divided into 4 subsystems: a) Instrumentation Hardware, b) Software, c) Manufacturing Interface & Modeling, and d) Probing Hardware a) Instrumentation Hardware The instrumentation hardware subsystem is responsible for interfacing with the probing system switching series (current) resistors in the circuit and voltage and phase measurements (which are, in turn, translated to real and imaginary impedance characteristics in software). There are three basic subunits in the preferred instrumentation subsystem as shown in FIG. 1: 1) Stanford Research Systems SRS810 1, 2) the interface board 2, and 3) Personal Computer 3 (486-xx) with IEEE-488 4 and digital I/O capability 5. The SRS 810 1 is computer controlled via the IEEE-488 bus 6 and is responsible for making voltage and phase measurements. The interface board is responsible for switching known resistor in series with the solder paste (for current measurements) and providing an interface for 2, 3, and 4 pole probes to the SRS810 1. The computer 3 is responsible for logic associated with controlling the time constant, resolution, filtering, frequency selection, voltage measurements, and phase measurements. The computer 3 processes the voltage and phase information to create a real and imaginary impedance characteristic. In addition, the computer 3 provides the relay firing logic that places the appropriate series resistor in the circuit for current measurements (magnitude and phase) and for voltage measurements across the solder paste or residue material (magnitude and phase). The computer 3 uses the National Instruments PC-DIO-24 digital I/O card 5 to send the logic for controlling the relays. See FIG. 2 for an detailed schematic of the interface card 2.

The Stanford Research System SRS 810 1 is an off-the-shelf lock-in amplifier that is capable of a) generating sine and TTL signals from 10 mHz to 100 kHz and b) making voltage and phase measurements in reference to the internally generated signal or an external signal. In addition, the SRS 810 1 has the capability of implementing different time constants, discrete resolution, and filtering options.

The computer 3 is responsible for implementing stored logic to control the National Instruments PC-DIO-24digital input/output card 5 that ultimately controls the relay firing sequence during a test. The relay firing sequence used to select a series resistor for a particular measurement in the Solder Paste and Residue Measurement System. In addition to selecting the series resistor, the computer 3 is responsible for switching between the series resistor and the solder paste/residue sample in order to measure both voltage and current through the solder paste or residue. From these voltage and current readings, the real and imaginary impedance of the sample can be calculated. The calculations used are:

Measured Values   Known Values
$V_Z$  $\Phi_Z$  $V_R$  $\Phi_R$    $R_S$  $V_{Source}$ Calculated Values
System Current $$I_S = \frac{V_R \underline{/\Phi_R}}{R_S \underline{/0°}} = \frac{V_R}{R_S} \underline{/\Phi_R - 0°} = \frac{V_R}{R_S} \underline{/\Phi_R}$$

Sample Impedance $$Z_{Sample} = \frac{V_Z \underline{/\Phi_Z}}{V_R/R_S \underline{/\Phi_R}} = R_S\left(\frac{V_Z}{V_R}\right) \underline{/\Phi_Z - \Phi_R}$$

The computer 3 also is responsible for system calibration, data management, data analysis, data representation (i.e. graphing, etc.), and solder paste control calculations.

The interface board's 2 primary role is do a discrete switch of the input to the SRS 810 1, to place high resolution discrete resistors in the measurement circuit for current measurements, and to interface with the probing system 7 for measuring solder paste and residues. There are five main functional blocks of the interface card's 2: (1) the computer interface 20, (2) inputs and outputs from the Stanford Research model SR-810 lock-in amp (these inputs come into the interface board at A 28, 29 and B 30, 31, (3) the programmable load cell 40, (4) the relay switching and driver circuitry 45, and (5) the power supply 47.

Computer Interface

The computer interface 20 consists of a digital I/O card 21 similar to the National Instruments PC-DI/O-24 resident in the computer and connected via a 50 conductor cable 22 to the interface board. The interface cable 22 mates via an interlocking connector mounted to the back side of the board. The 50 lines are configured as 24 channels with separate grounds and a 5 volt output with ground. All the ground lines from this connector are tied to the system ground. The 24 single channel outputs are TTL logic compatible and buffered through inverters which actuate drivers for the relays which facilitate input mode, and load cell switching.

Instrument & Probe Interface

The probe interface 23 consists of four panel mounted test points (TP1–TP4) used to connect the probe and sample under test to the measurement system. TP1 24 is the Working electrode, TP2 25 is the Working Sense electrode, TP3 26 is the Reference electrode, and TP4 27 is the Counter electrode. The interface to the SR810 lock-in amplifier consists of 6 jacks: J1 28 connects to the A channel on amp 1, J2 29 to B channel on amp 1, J3 30 to A channel on amp 2, J4 31 to B channel on amp 2, J5 32 to Sine Out on amp 1, and J6 33 to Ref In on amp 2.

If two lock in amplifiers are used in the system (such as a lock in amp with a different frequency range), relays in the input switching relays 35 are used to select which lock-in amplifier is switched "in circuit" to perform the measurement. An additional connection is made from the sine out 32 of lock in amplifier one (master) to the Ref In 33 input on lock-in amplifier two (slave). The two inputs "A" 28 and "B" 29 form the differential input to the lock-in amp. The sine out 32 from the lock-in amp is used as the stimulus to the sample under test via TP1 24.

Relays in the input switching relays 35 are configured to connect input "A" 28 or 30 and "B" 29 or 31 to TP2 25 and TP3 26 in the de-energized position to facilitate the 4 pole voltage measurement. Relays in the input switching relays 35 are also configured to switch the "A" 28 or 30 input to TP3 26 and the "B" 29 or 31 input to LO side of the generator for the 4 pole current measurement.

Relays in the input switching relays 35 are also configured to switch the "A" 28 or 30 input to TP1 24, and the "B" 29 or 31 input to TP4 27 to configure the system for a 2 pole voltage measurement (This measurement is only made when the solder paste impedance is <500 KW). The 2 pole current measurement is facilitated by energizing the input switching relays 35 to connect the "A" input 28, 30 to TP4 27 and the "B" 29 or 31 input to the LO side of the generator.

Relay in the input switching relays 35 switch the "A" input 28 or 30 to TP3 26 and the "B" input 29 or 31 to TP4 27 to facilitate a 3 pole voltage measurement. This places the analyzer inputs across the probe interface. By energizing the input switching relays 35 to connect the "A" input 28 or 30 to TP4 27 and the "B" input 29 or 31 to the LO side of the generator facilitates the 3 pole current measurement.

In the test mode, only one of the five input switching relays will be activated at any one time. Relays in the input switching relays 35 are tied in a parallel configuration and are actuated as one 4-pole double-throw relay. These set of relays switch the measurement from lock-in amplifier number one (Master) to lock in amplifier number two (Slave). A relay in the input switching relays 35 will switch the measurement system to a 3 pole voltage configuration. And a relay must be de-energized prior to changing the input switching mode. A relay will also switch the system to a 2 pole voltage configuration, and must be de activated prior to changing input switching modes. Relays in the input switching relays 35 will switch the measurement system to the 2, 3, or 4 pole current mode, and de-activated will switch to the 4 pole voltage mode. With no mode relays activated, the system is in the 4 pole voltage mode. One relay in the input switching relays 35 always switches the analyzer inputs to measure the voltage drop across the load resistor(s) selected in the load cell.

Programmable Load Cell

The programmable load cell 40 consists of 20 Single-Pole Single-Throw (SPST) high quality relays 41 that are connected to TP4 27 and input mode switching relays 35. There are 20 precision load resistors 42, one each for the 20 relays in the cell. The resistors are connected to the normally open terminal of the relays. These relays can be activated to switch the resistors "in circuit" individually, or in parallel combinations to program the required load resistance. Load cell resistance ranges can be tailored to fit specific applications by adjusting the values.

Relays for the load resistors 41 are used for load cell switching. The load cell switching is straight forward, with no relays activated no load resistor is selected and the load value is an open circuit. By energizing the required relay or set of relays, one can obtain a large range of load values.

Relay Switching and Driver Circuitry

Relay switching and driver circuitry 45 is controlled by the TTL logic supplied from the digital I/O card 5 resident in the computer 3. There are four test modes. Control channels (lines) from the I/O card control this mode switching. These control lines are connected to the relay driver circuitry 46 via inverters to buffer the TTL logic to the low impedance of the relay drivers.

Load cell relay switching is controlled by the I/O card control lines. These control lines are connected to five 14 pin LM3146 transistor arrays in the relay driver circuitry 46. When these are activated, current is supplied to the relay coil, switching "in circuit" the load resistor selected. The driver devices and relays can be programmed with the computer and I/O card to select desired load values using single resistor elements or by programming parallel resistor combinations to obtain the required load value.

The driver circuitry for the relays is configured to minimize electrical noise by switching the current in the ground leg instead of switching the high side of the supply current. The load cell is laid out in a "U" configuration to keep the load resistors and control circuitry as close to the probe jack inputs as possible. Input mode switching relays, inputs from the analyzer, and probe input jacks will employ topography and layout considerations to minimize electrical interactions.

Power Supply

The interface board was designed to minimize power requirements from the supply. However the power requirements exceed those of the computer and an external one is needed. The on-board power supply consists of an LM 317 T, or 117 T three terminal adjustable regulator, heat sink, and associated circuitry. The input voltage to this regulator circuit is supplied via an AC to DC converter and cable with a standard 5.0 mm plug and mating jack mounted to the interface board. This converter will have a rating between 14.5 and 16 VDC @ 800 mA to 1.0 A.

The input is filtered by two capacitors in parallel and connected to the input terminal of the LM 317 T. The potentiometer and capacitor in the control leg of the regulator sets the output voltage and reduces the ripple voltage at the output. The diode and capacitor on the output leg is to protect the regulator from a short circuit and to filter the output voltage.

b) Software

Figure 3:
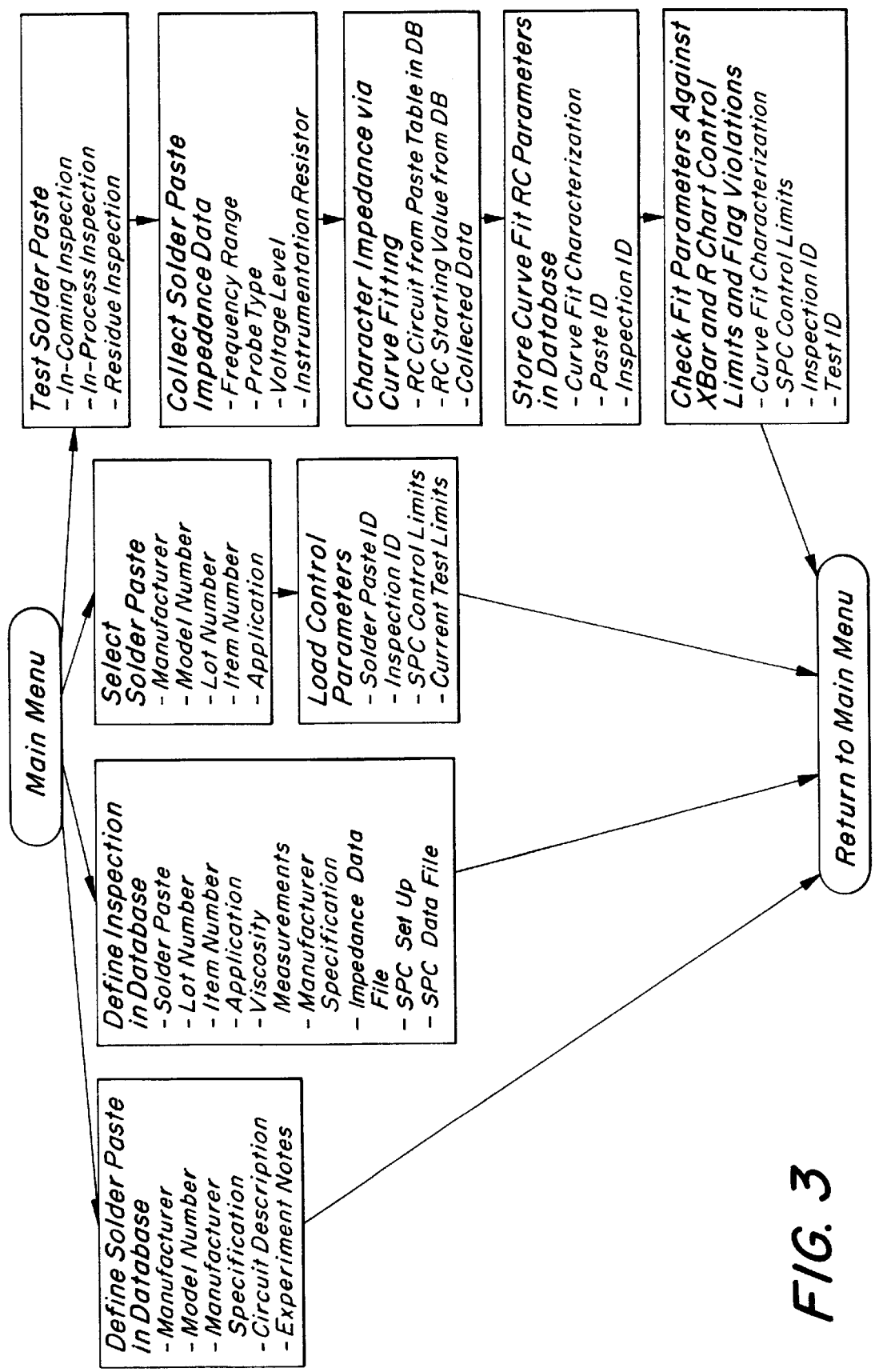
FIG. 3 is the Basic Menu Functionality of the Solder Process Control Software

The Solder Paste and Residue Measurement System software controls the hardware used for collecting impedance data from a solder paste sample. In the preferred embodiment the software is a menu driven software package which provides the user the ability to utilize a database for setup, and result storage, and to collect and analyze impedance data. The basic functionality of the system is illustrated in FIG. 3.

The first menu item allows the user to setup the Solder Paste in the database. This information is stored in the Solder Paste Table in the database. The information which may be defined within this table includes the Manufacturer, Model Number, Manufacturer's Specification, Circuit Description, and Experimental Notes. The Manufacturer and Model Number identify this record in the database. The circuit description is used to characterize the solder paste.

The second menu item allows the user to define the inspections which will occur on the solder paste. The information which may be entered includes the Solder Paste ID (Manufacturer and Model Number), Lot Number, Item Number, Application, Viscosity Measurements, Manufacturer's Specifications, Impedance Data File, solder paste control (SPC) Setup, SPC Data File. Each record in the inspection table is identified by the Solder Paste ID, Lot Number, Item Number and application. The Impedance Data File specifies the data file which will store the measured impedance data. The SPC Data File describes the name of the data file which represents the control limits for the X-Bar and R charts.

The third menu allows the user to select a solder paste inspection. Each inspection is uniquely identified by the Manufacturer, Model Number, Lot Number, Item Number and Application. Once the user has selected a solder paste the control parameters are loaded into the global memory so that other features of the software may use them. The control parameters which are loaded include the Solder Paste ID, Inspection ID, SPC Control Limits and Current Test Number.

The fourth menu allows the user to perform a test on the solder paste. The first action required is to collect the data from meter over a variety of frequencies. The following must be specified to collect data, Frequency Range, Probe Type, Voltage Level, Instrumentation Resistor. Once the data is collected it is characterized by curve fitting the data to the circuit description defined in the solder paste table. The solder paste table supplies the circuit description and the starting values. The curve fit is a modified Marquardt-Levenberg non-linear least squares fit. The resulting parameters from the curve fit are then stored in the database in a record which is related to the Inspection ID. The software then reviews the current and previous results and calculates the SPC limits. If a control limit is violated the software then indicates this to the user.

The Executive Module controls the main menu, multiple document interface, file import/export, and printers. The Paste Database Module controls access the system database. The Data Collection Module controls the data collection of the system. The Curve Fit Module provides the curve fitting functionality. The RC Circuit Values Module provides SPC control limit checking of X-Bar and R chart limits of specified circuit parameters.

Solder Paste and Residue Measurement System Software Flow Chart Description

Figure 4:
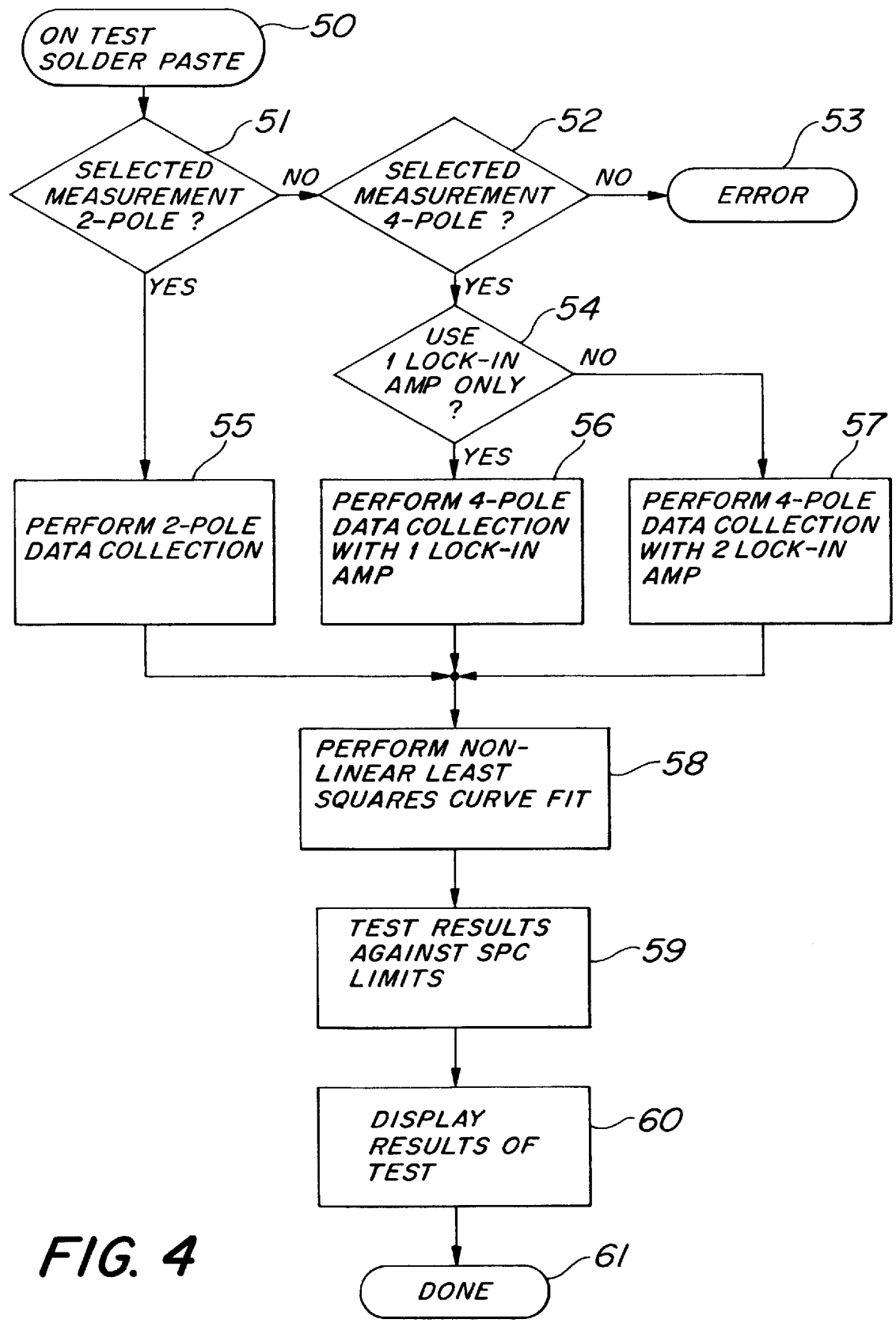
FIG. 4 is the Master Flow Chart of Impedance Spectroscopy Measurements

The master flow chart of the solder paste and residue measurement system is shown in FIG. 4. At the start of the solder paste test sequence the user must select either a 2 or 4 pole measurement scheme. 51, 52.

Figure 5:
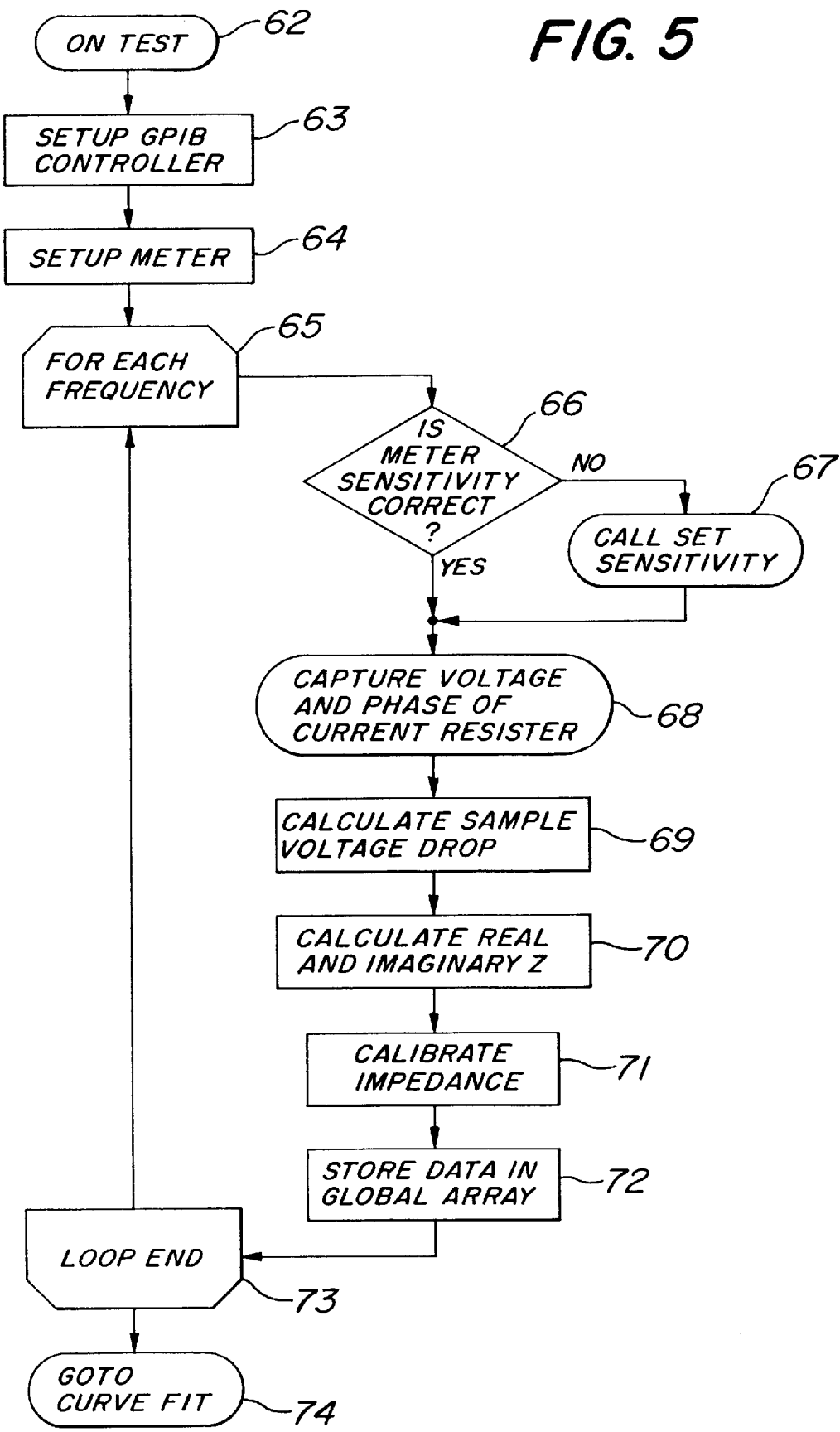
FIG. 5 is the Data collection flow chart for the 2-pole measurements

A flow chart of the data collection for 2-pole measurements is shown if FIG. 5. The first step in the 2-pole measurement is setting up the GPIB controlled 63 within the computer. This is accomplished to initiate handshaking protocol for future controller communication. The next step is to setup the SR810 64. This step sends data, such as user selected voltage levels, low-pass filter settings, front-end coupling information, and grounding configuration. After initial set-up, the meter begins to step through the user selected frequencies and collects real and imaginary impedance using the following process:

Determine if the meter sensitivity is properly set 66.

(Meter sensitivity is a gain setting on the front end of the meter.)

If the sensitivity is set too low, the front-end amplifier will saturate, if set too high, the measurement will not be made at an optimum resolution.

If the meter sensitivity is too low or too high, make appropriate changes to establish an optimum sensitivity setting.

Figure 8:
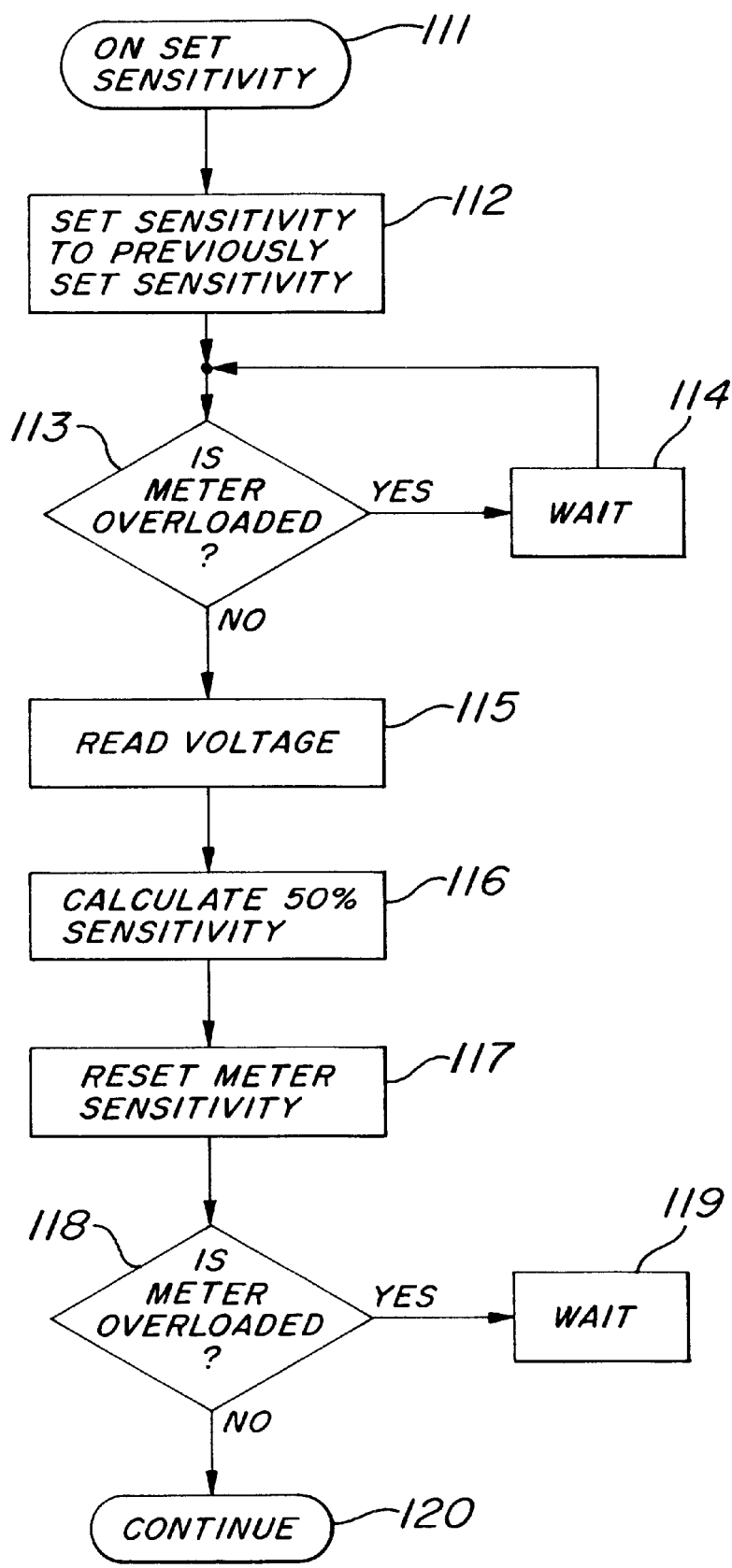
FIG. 8 is the set sensitivity flow chart

(The sensitivity setting flow chart is shown in FIG. 8. The first step is to set the sensitivity of the meter to the previously set sensitivity for either the current of voltage, depending on the measurement being made. 112 Then determine if the meter is in overload (i.e. the front-end amplifiers are saturated) 113. If yes (meter is overloaded), then wait to allow for meter settling, and adjust sensitivity to the highest setting and re-assess overload condition 114. If no, continue and capture RMS voltage 115, calculate the sensitivity setting that will provide a near 50% sensitivity 116 and reset meter sensitivity to this new sensitivity setting and ensure that the meter does not overload as a final check 117.)

Figure 9:
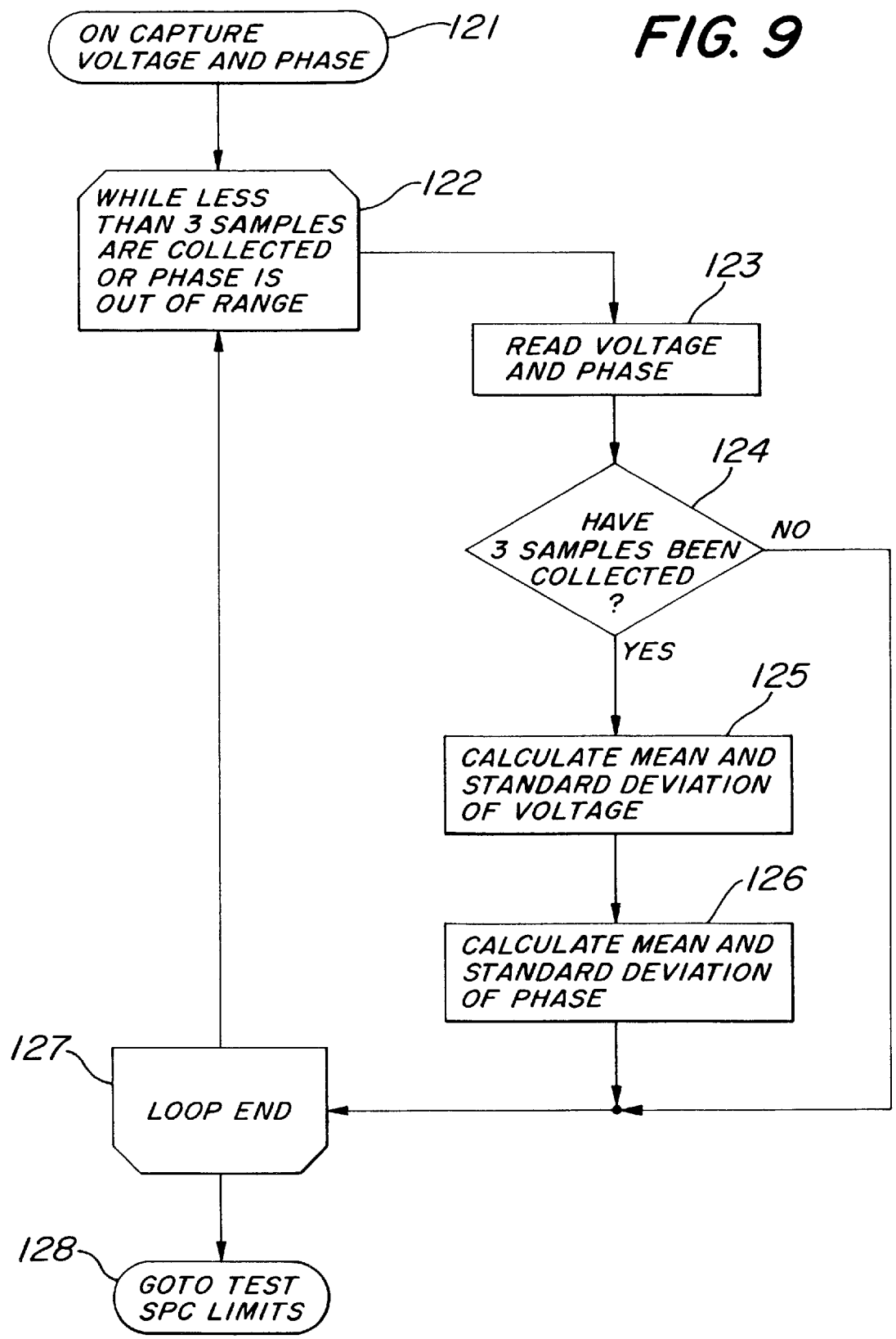
FIG. 9 is the flow chart for the capture voltage and phase

Continuing with in FIG. 5 with the steps required for data collection for 2-pole measurements the next step is to capture the voltage and phase from the series (current sensing) resistor that resides in the interface board 68. The voltage and phase capturing logic is shown in FIG. 9. First three voltage and phase samples are read 123, 124. Then the mean and standard deviation of these measurements are calculated 125. If the mean falls within a defined number of standard deviations, then, continue or else, Loop back to step 1, 122.

Then on the data collection for 2- pole measurements, FIG. 5 the sample voltage drop are calculated using a voltage divider logic scheme 69, the real and imaginary impedance of the sample are calculated given the measured current (from the series resistor) and the calculated voltage across the sample 70, the impedance is calculated 71, if necessary and the results are stored in a global array (RAM) 72.

Referring back to the master flow chart FIG. 4 if the 4-pole measurement scheme is selected, then the user must select either 1 or 2 lock-in amplifiers. The preferred Solder Paste and Residue Measurement System data collection in the 4-pole mode can be made with either 1 or two lock-in amps (1 measures current, the other voltage).

Figure 6A:
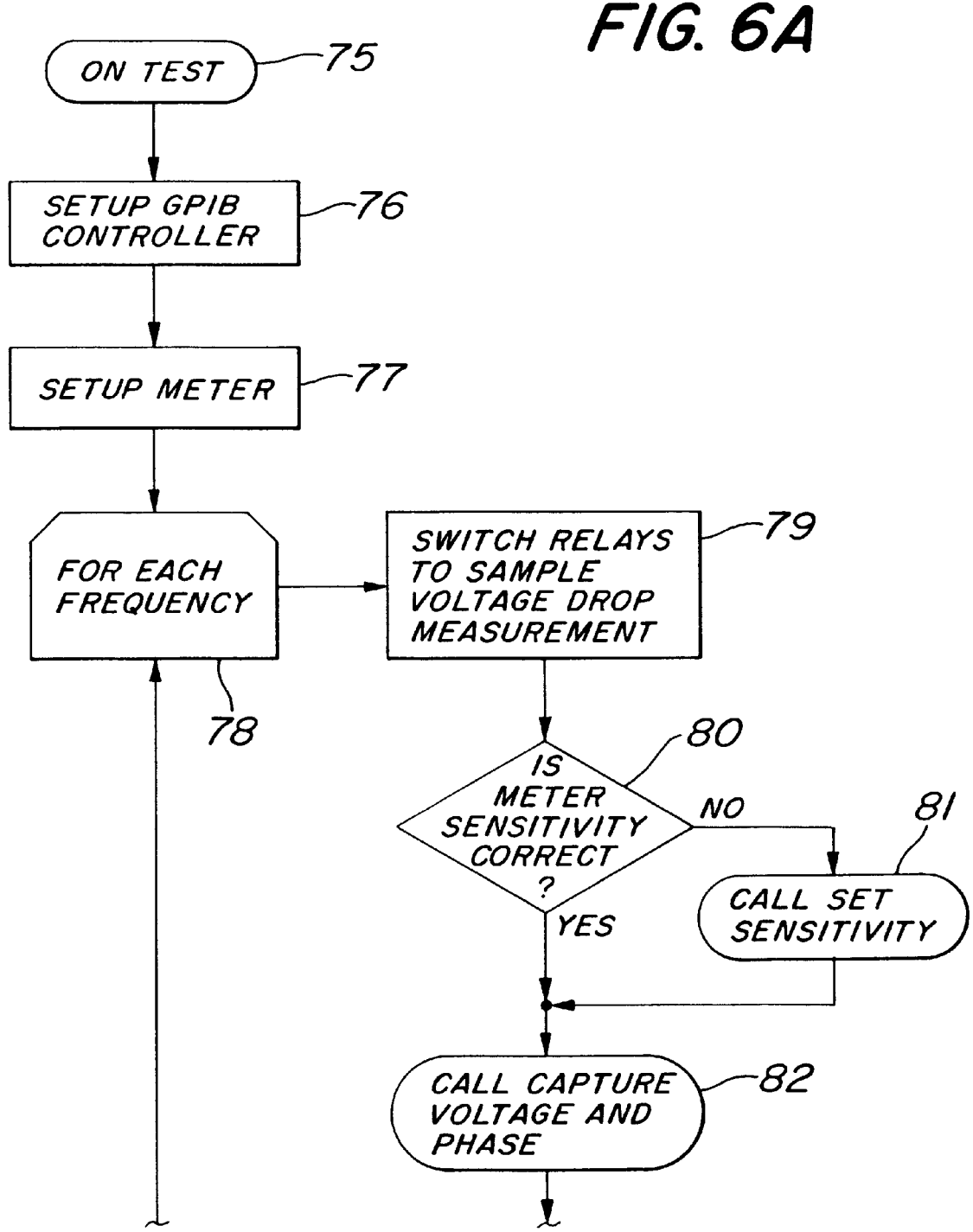
FIGS. 6A–B is the data collection flow chart for the 4-pole measurements with one lock-in amp
Figure 6B:
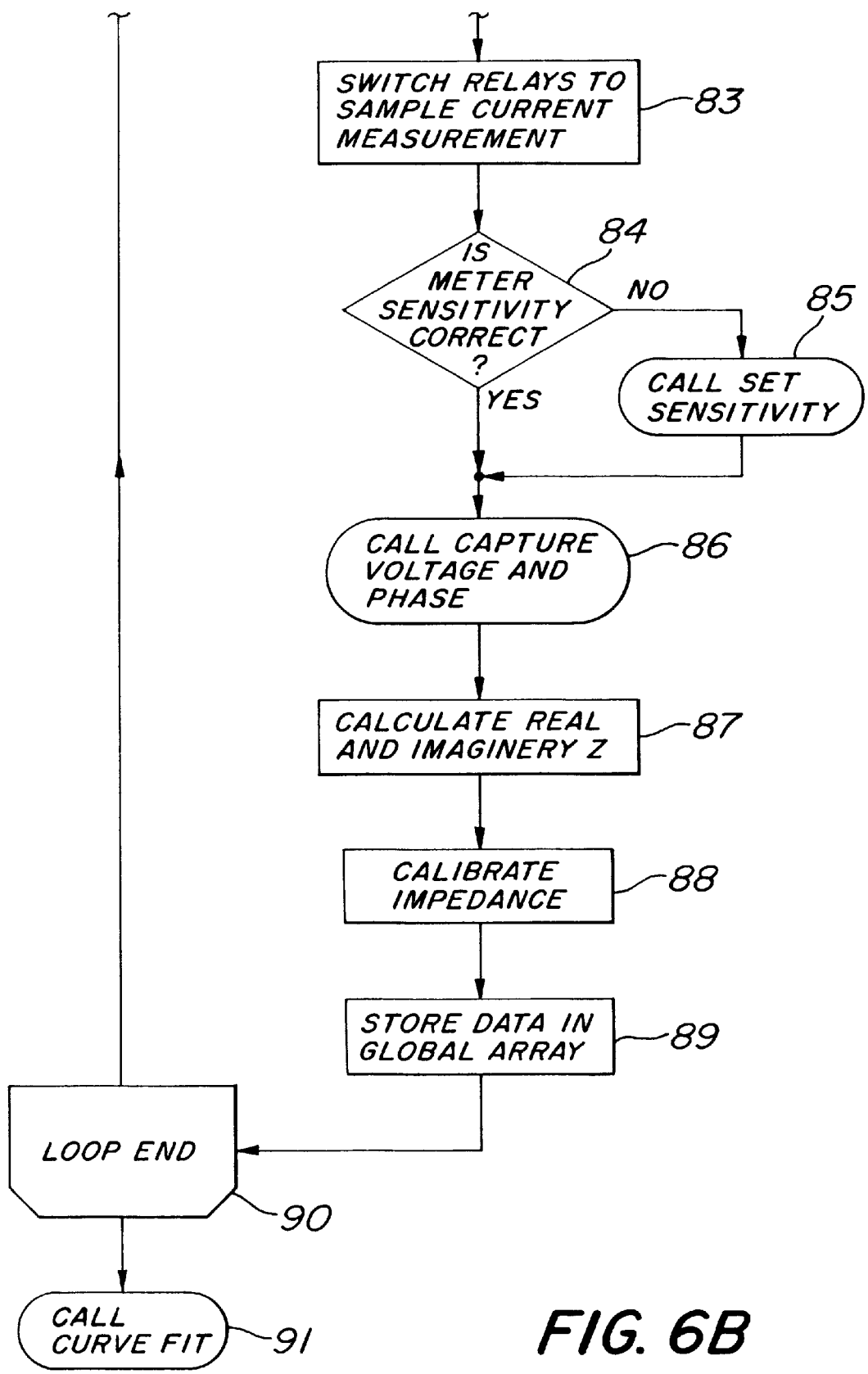

In FIG. 6A–B the 4-pole, 1 amp collection is shown. The first step in the 4-pole measurement, as was with the 2-pole measurement, is setting up the GPIB controlled within the computer 76. This is accomplished to initiate Handshaking protocol for future controller communication. The next step is to setup the SR810 77. This step sends data, such as user selected voltage levels, low-pass filter settings, front-end coupling information, and grounding configuration. After initial set-up, the meter begins to step through the user selected frequencies and collects real and imaginary impedance using the following process:

Switch relays in the interface board to allow for a sample voltage drop and phase measurement from the voltage sensing electrodes 79.

Determine if the meter sensitivity is properly set 80.

(Meter sensitivity is a gain setting on the front end of the meter. If the sensitivity is set too low, the front-end amplifier will saturate, if set too high, the measurement will not be made at an optimum resolution. If the meter sensitivity is too low or too high, make appropriate changes to establish an optimum sensitivity setting. Refer to FIG. 8 and discussion supra for more details regarding sensitivity setting logic 81.)

Capture the voltage and phase from the voltage sensing electrodes 82 (for voltage and phase capturing logic, refer to FIG. 9 and discussion supra).

Switch relays in the interface board to allow for a sample current and associated phase measurement 83.

Determine if the meter sensitivity is properly set 84.

(Meter sensitivity is a gain setting on the front end of the meter. If the sensitivity is set too low, the front-end amplifier will saturate, if set too high, the measurement will not be made at an optimum resolution. If the meter sensitivity is too low or too high, make appropriate changes to establish an optimum sensitivity setting. Refer to FIG. 8 and discussion supra for more details regarding sensitivity setting logic.)

Capture the voltage and phase from the series 86 (current sensing) resistor that resides in the interface board (FIG. 9). This is the magnitude and phase of the current flowing through the sample.

Calculate the real and imaginary impedance 87 using the sample voltage and current measurements as described above.

Calibrate the impedance 88, if necessary.

Store data in a global array 89 (RAM).

Figure 7A:
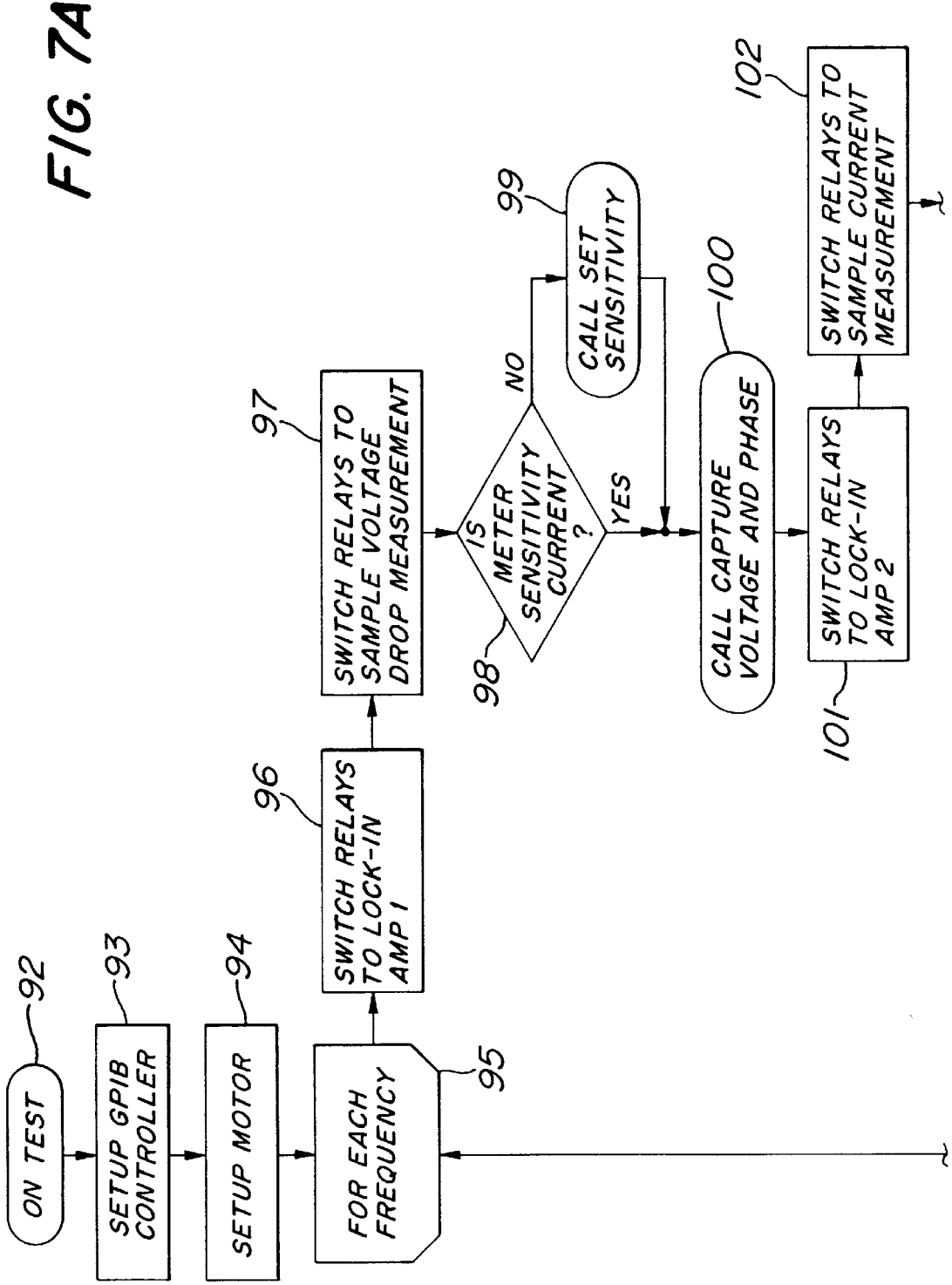
FIGS. 7A–B is the data collection flow chart for the 4-pole measurements with two lock-in amps
Figure 7B:
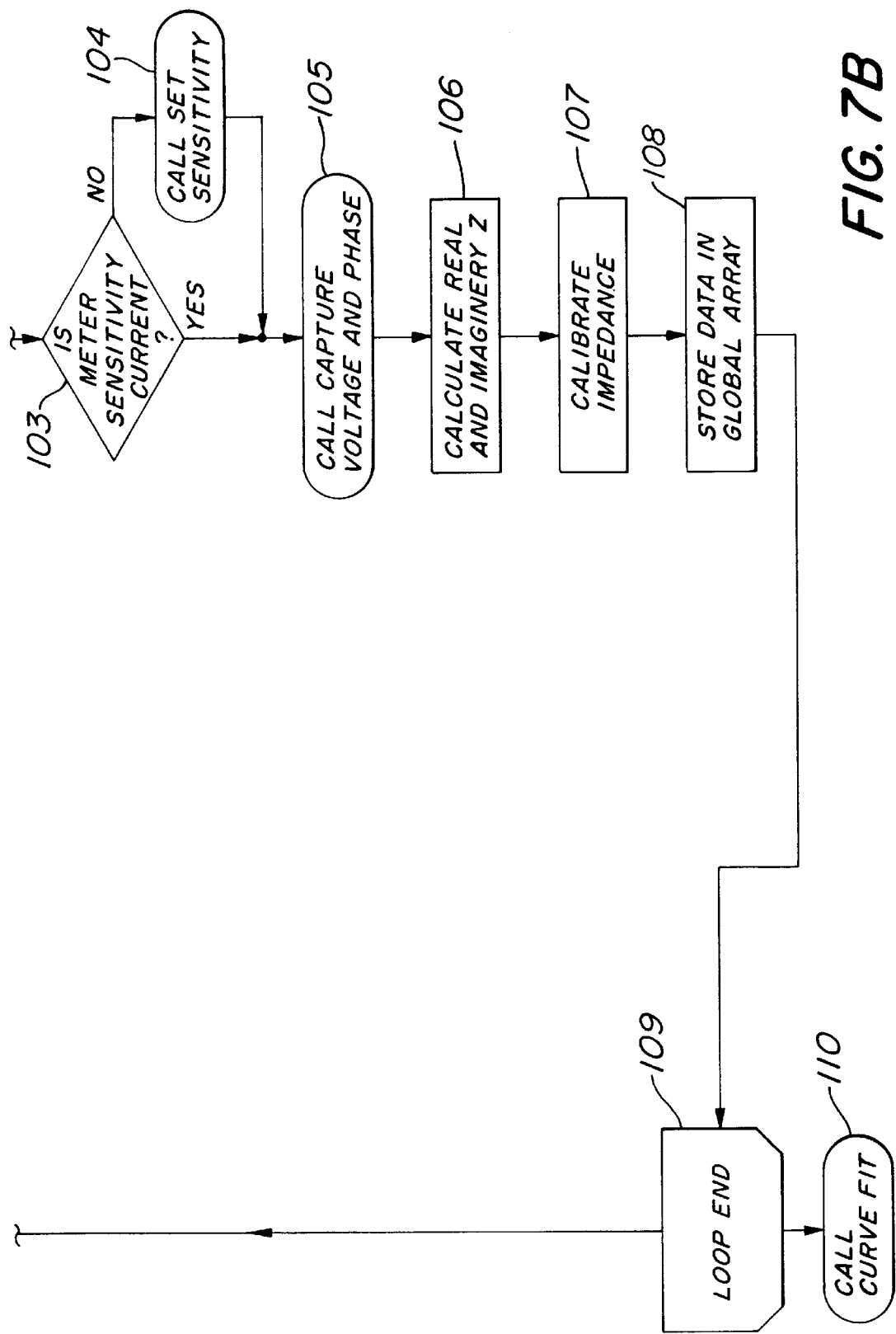

For 4-pole, 2 amp collection, refer to FIG. 7A–B. The first step in the 4-pole measurement, as was with the 2-pole measurement, is setting up the GPIB controlled within the computer 93. This is accomplished to initiate Handshaking protocol for future controller communication. The next step is to setup the SR810 94. This step sends data, such as user selected voltage levels, low-pass filter settings, front-end coupling information, and grounding configuration. After initial set-up, the meter begins to step through the user selected frequencies and collects real and imaginary impedance using the following process:

Switch relays in the interface board measure voltage and phase data from Lock-In Amp #1 96.

Determine if the meter sensitivity is properly set 98. (See FIG. 8 and discussion supra.)

Capture the voltage and phase from the voltage sensing 100. (See FIG. 9 and discussion supra.)

Switch relays in the interface board measure voltage and phase data from Lock-In Amp #2 101.

Switch relays in the interface board to allow for a sample current and associated phase measurement 102.

And once again determine if the meter sensitivity is properly set. (FIG. 8 and discussion supra.)

Capture the voltage and phase from the series (current sensing) resistor that resides in the interface board 105. This is the magnitude and phase of the current flowing through the sample.

Calculate the real and imaginary impedance using the sample voltage and current measurements as described supra 106.

Calibrate the impedance 107, if necessary.

Store data in a global array (RAM) 108.

Figure 10:
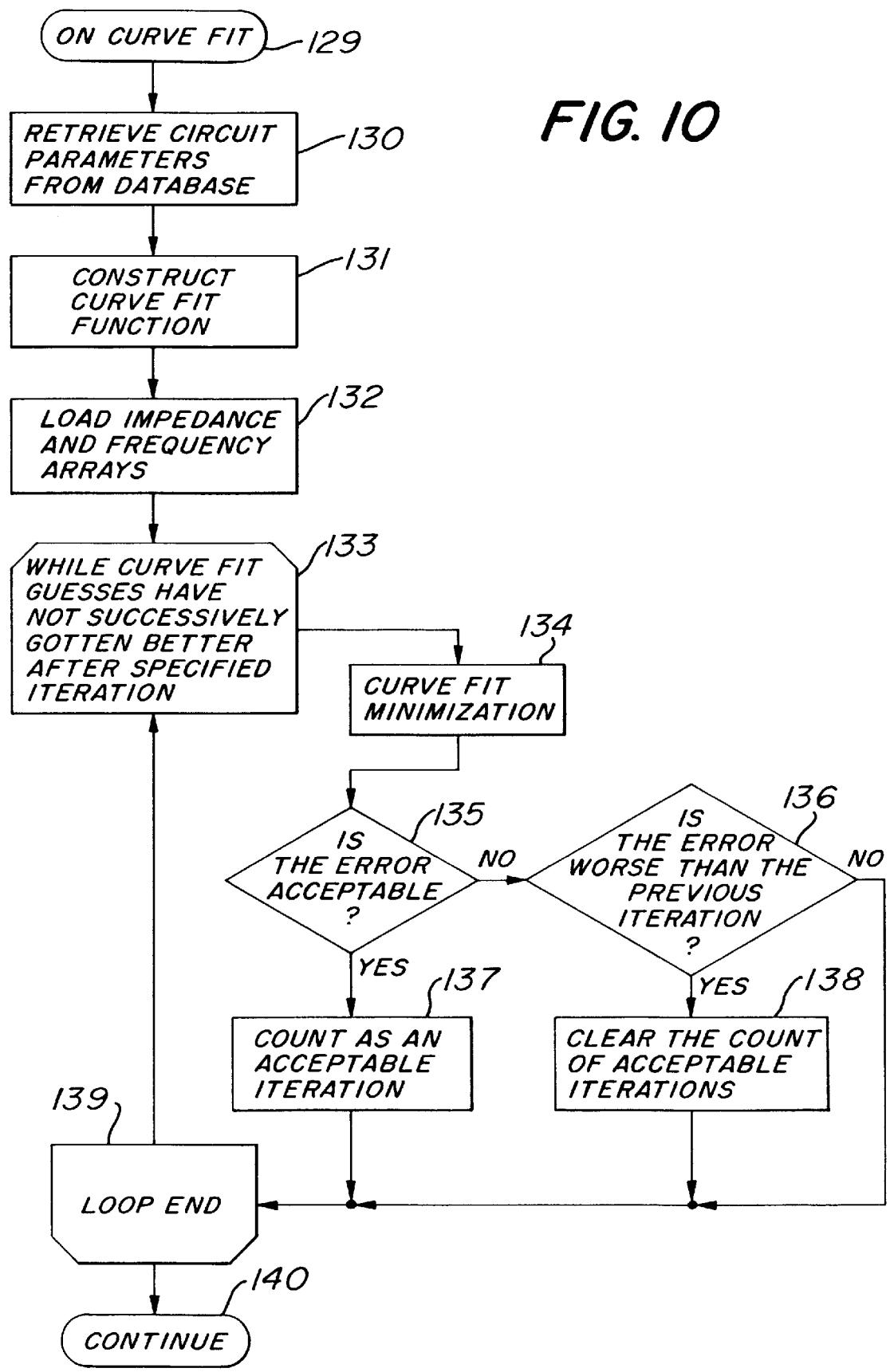
FIG. 10 is the flow chart for the non linear least squares curve fit
Figure 11A:
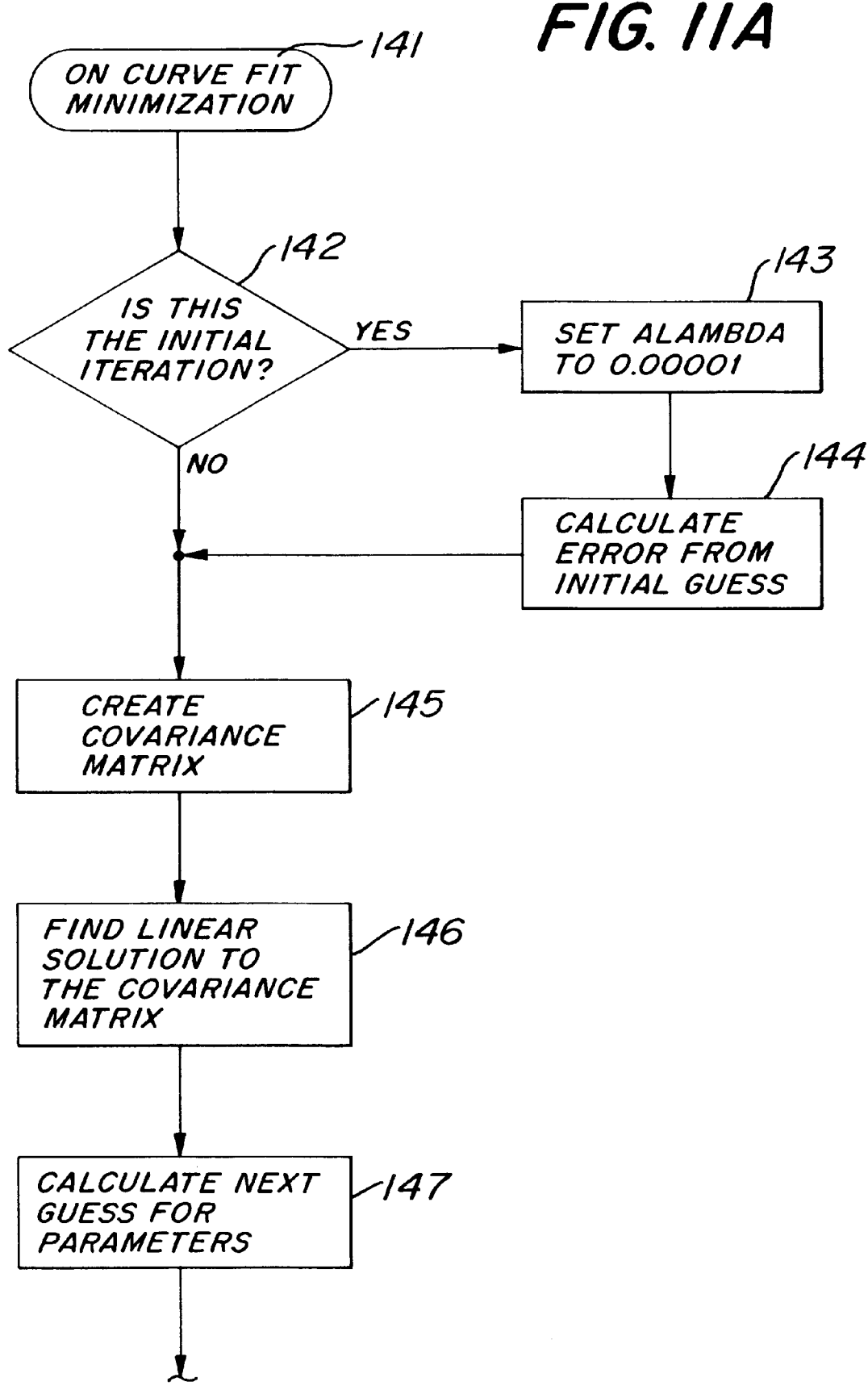
FIGS. 11A–B are the flow chart for the curve fit minimization (Marquardt-Levenberg method)
Figure 11B:
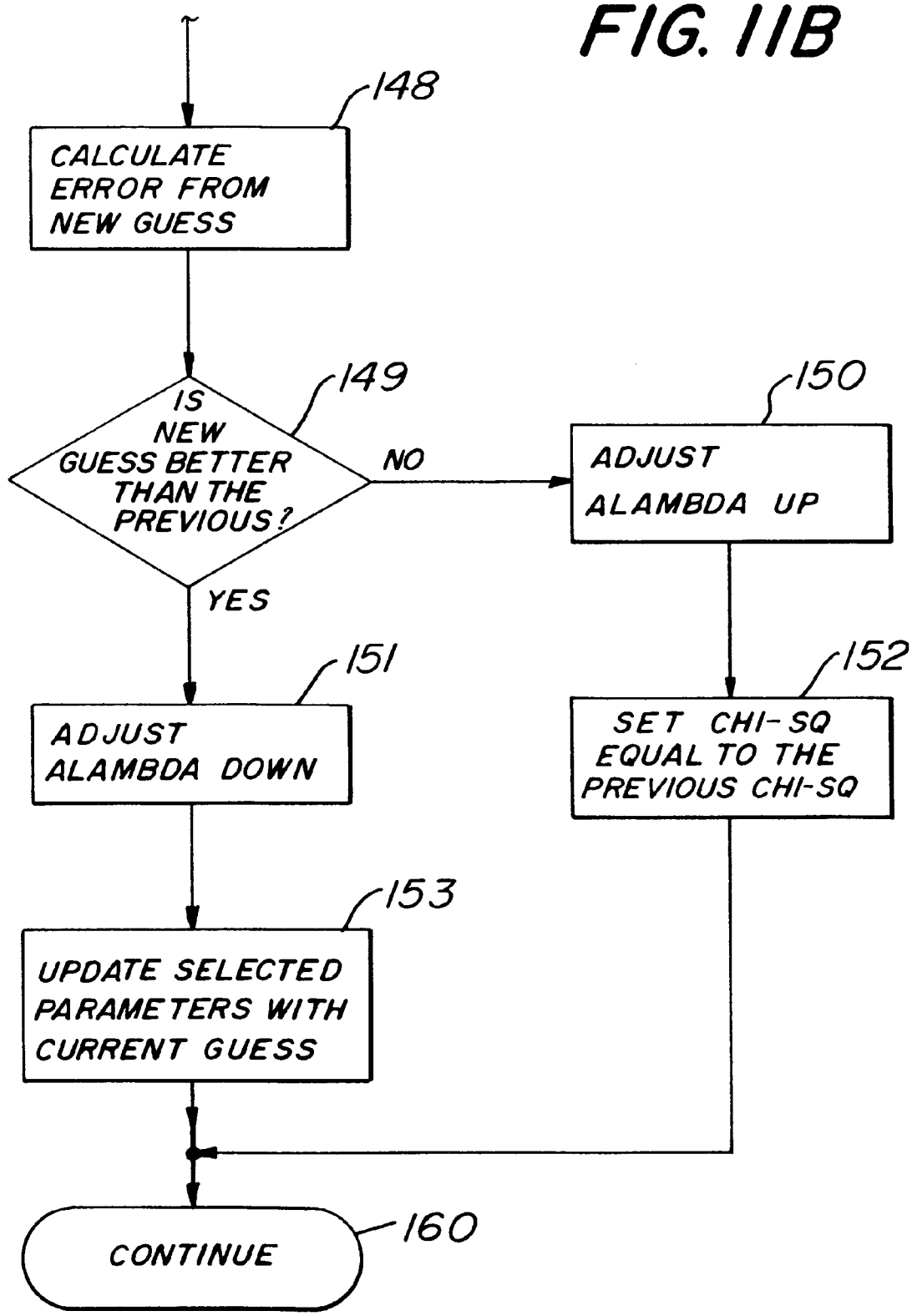

Back to FIG. 4, that master flow chart, once the data is collected, it is analyzed using Complex Nonlinear Least Squares (CNLS) Curve Fitting Analysis. The logic of this portion of the software is shown in FIG. 10. After the collected data is retrieve the following data from the data base 130 the circuit structure is determined (i.e. series & parallel construction of the resistors and capacitors) and the starting values from which the iterative curve fitting process will commence are determined. A mathematical function is constructed 131 from the circuit structure provided that calculates the real and imaginary impedance. The impedance data from the solder paste test is loaded into arrays 132 and using the constructed mathematical function and the collected data, enter the curve fit minimization algorithm (Marquardt-Levenberg Method) 134. This minimization method is described in FIG. 11A–B. In the first iteration, the variable alambda is set to 0.00001 143 and the error (chi-square) is calculated 144 from the starting values provided from the data base. If this is not the initial iteration continue to 145. A covariance matrix is created 145 and a linear solution to the covariance matrix (Gauss-Jordan is used) is found 146. The next guess for the parameters (This is accomplished using the solution to the covariance matrix and the alambda value.) is then calculated 147 and the error (chi-square) using the new set of estimated parameters is calculated 148. At this point, at 149, the new set of estimated parameters are tested to determine if the error has decreased. If the new guess lowers the error alambda is adjusted down 151, if the new guess does not lower the error alambda is adjusted up 150 and the chi-square (error) is set 152 to the chi-square of the previous iteration. Finally, the selected parameters are adjusted with current guess and the process continues. From this curve fit minimization algorithm, error (chi-square) and estimated component parameters are provided.

Continuing with FIG. 10, the non-linear least squares curve fit, after the curve fit algorithm described supra the program logic enters the decision block 135 and the error from the Marquardt-Levenberg is determined to be acceptable or unacceptable. If the error is acceptable the error is calculated from the Covariance Matrix, store estimated parameter values, and count as an acceptable interation 137. The program than loops back to 133 until the number of specified iterations are met with no change in error and the iterative changes for each parameter are oscillating. If the error from the non-linear least squares curve fit algorithm is not acceptable then determine if the error is worse than the previous iteration? If it is not then clear the count of acceptable iterations and go to 133, otherwise go directly to 133

Figure 12A:
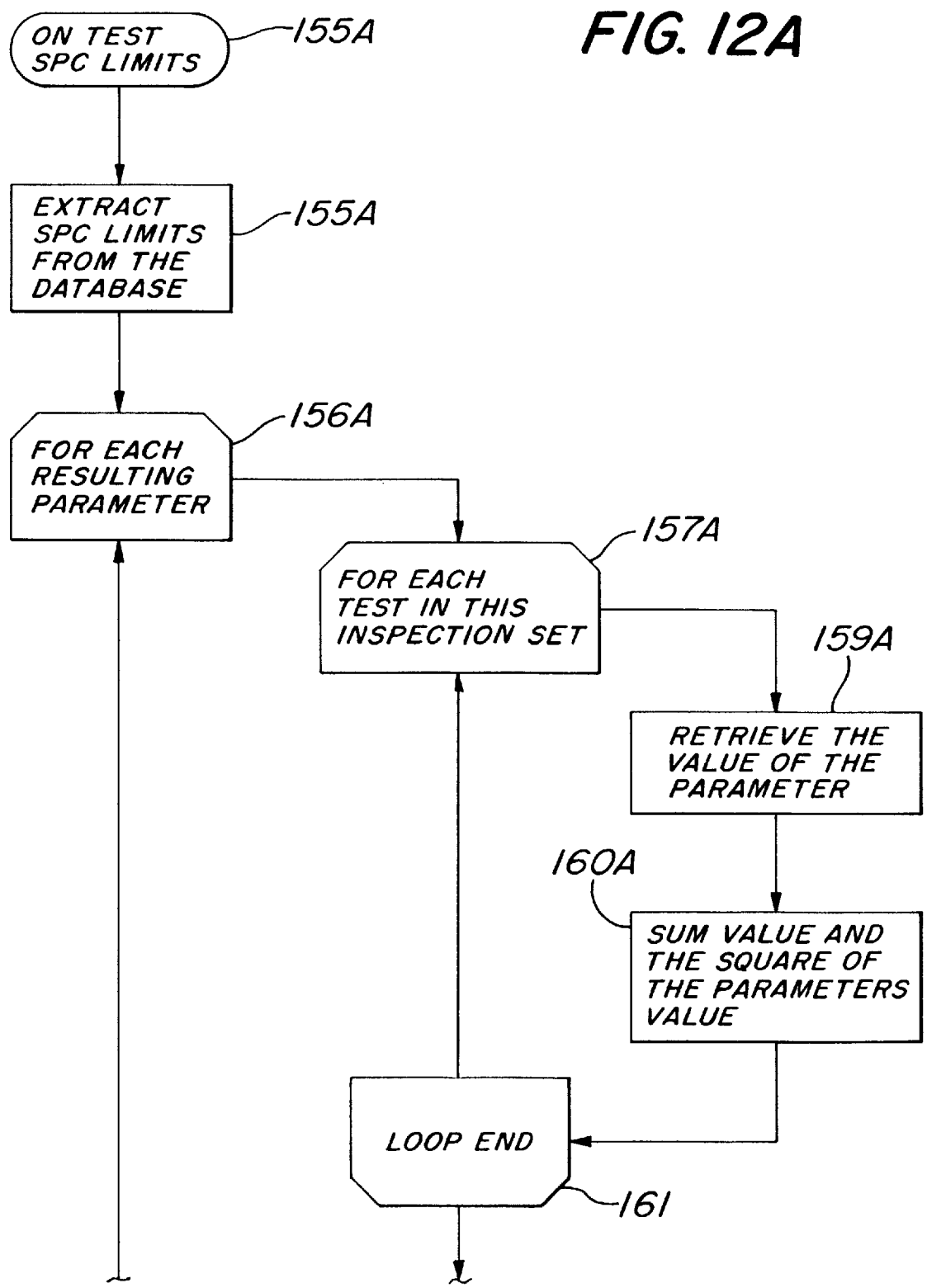
FIG. 12A–B are the flow chart for the test statistical process control limits
Figure 12B:
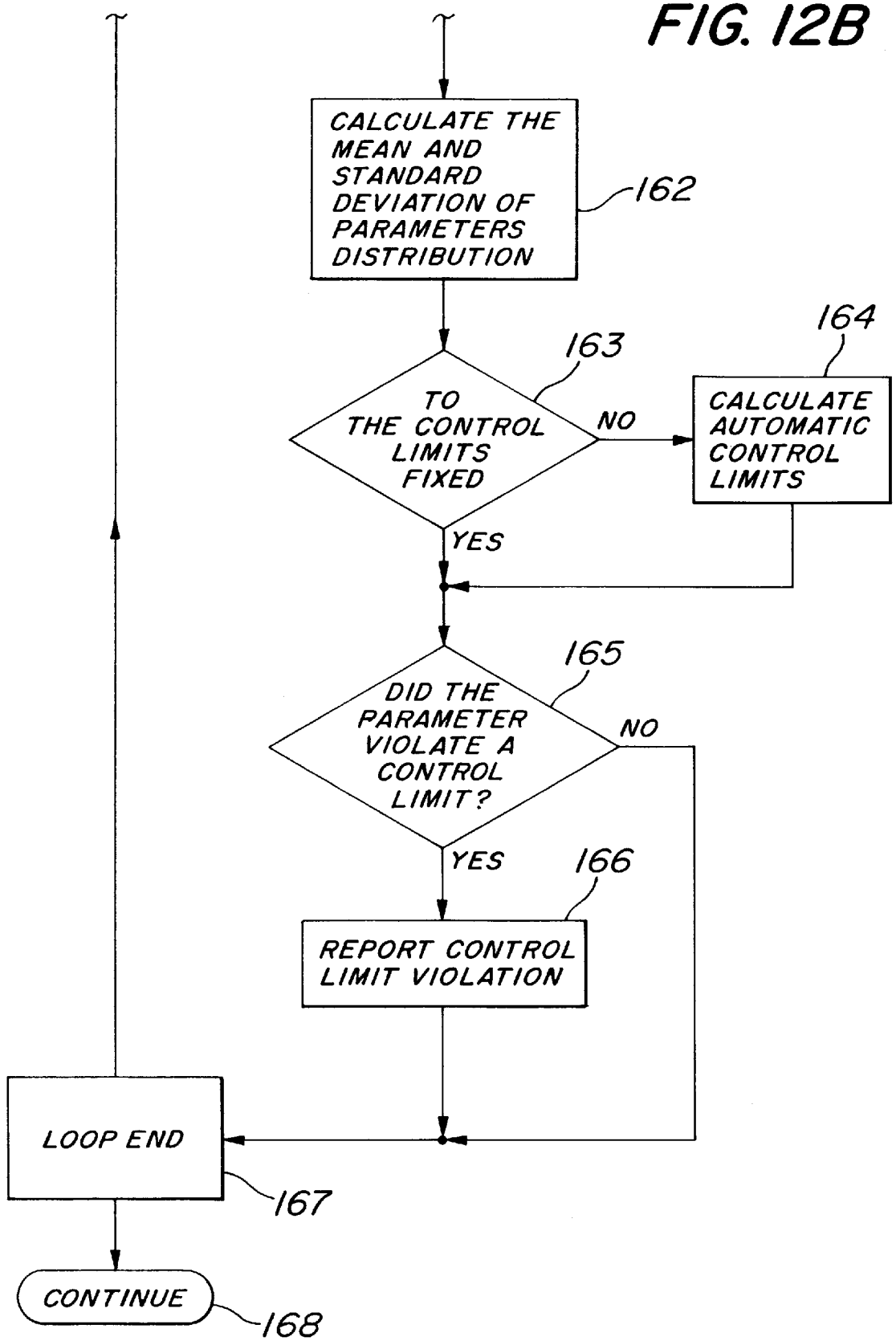

After the data is analyzed using the CNLS analysis techniques, best-fit circuit parameter are generated that are compared with the user defined Statistical Process Control (SPC) limits. FIG. 12A–B shows the flow chart for testing the SPC limits. The first step in this testing is to extract the current SPC limits from the data base 156. Then for each of the parameters selected for a specific component configuration for a specific solder paste do the following, (Note: this is used to develop the SPC charts—X-Bar and R Charts):

For every test in the inspection set for a particular solder paste 157A, retrieve the estimated value for the parameter 159A. Calculate the sum, the sum of squares, and the square of the estimated parameter value for the inspection set 160A. Calculate the Sample Mean and the Standard Deviation 162 and determine if the control limits fixed by the user have been surpassed 163? If they have continue to 165. If they have not then calculate the control limits based on the sample mean, standard deviation, and the user selected K value (K values are used in SPC systems to expand and contract the control of a process) 164. Finally the parameter collected from a specific test is tested to determine if it violates the control limits and if it has the violation is reported 166 otherwise the program loops back to 157 till all parameters have been tested.

In the final stage in the master flow chart, FIG. 4, the results of the test are displayed and stored in the data base 60 and the program and impedance spectroscopy measurement has completed.

c) Manufacturing Interface & Modeling

The utility of using impedance spectroscopy on solder paste and residue materials is to provide more control in their use in manufacturing. Solder paste specifically is a very dynamic material that can readily deteriorate within a single shift in manufacturing. A generic list of solder paste failure modes is as follows:

a) Moisture absorption causing excessive powder oxidation and solder balling b) Changes in rheologic properties (Viscosity and Thixotropic Index)

c) Increased powder oxidation state d) Inactivation or immobility of the activator Therefore, in order for this system to be implemented as an solder process control (SPC) device for solder paste, there must be strong correlations between the data generated by this measurements system and the behavior of solder paste in manufacturing. In order to provide this level of correlation both linear regression techniques and probabilistic failure analysis techniques were employed.

Figure 13:
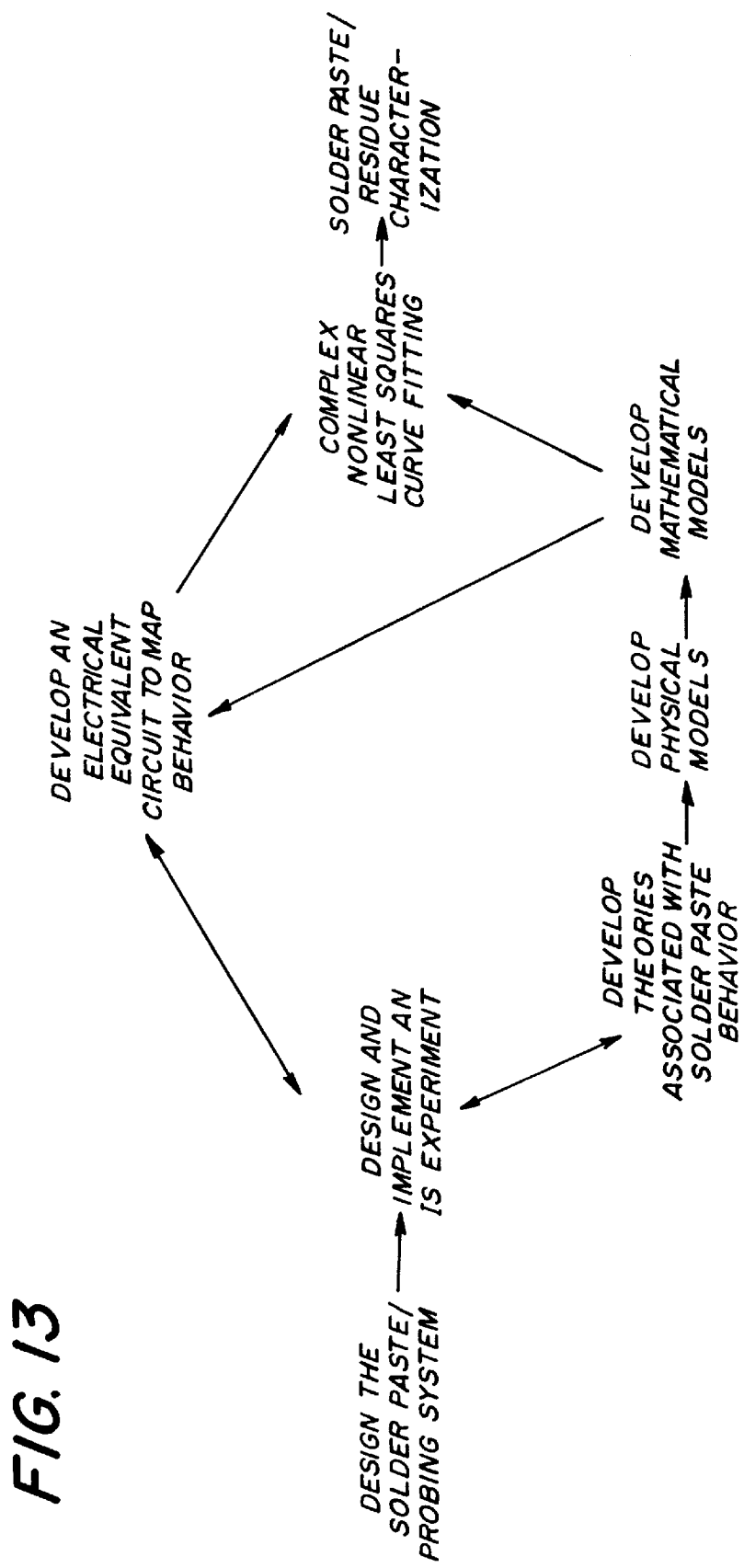
FIG. 13 shows the approach used to characterized solder paste material using impedance spectroscopy techniques
Figure 14:
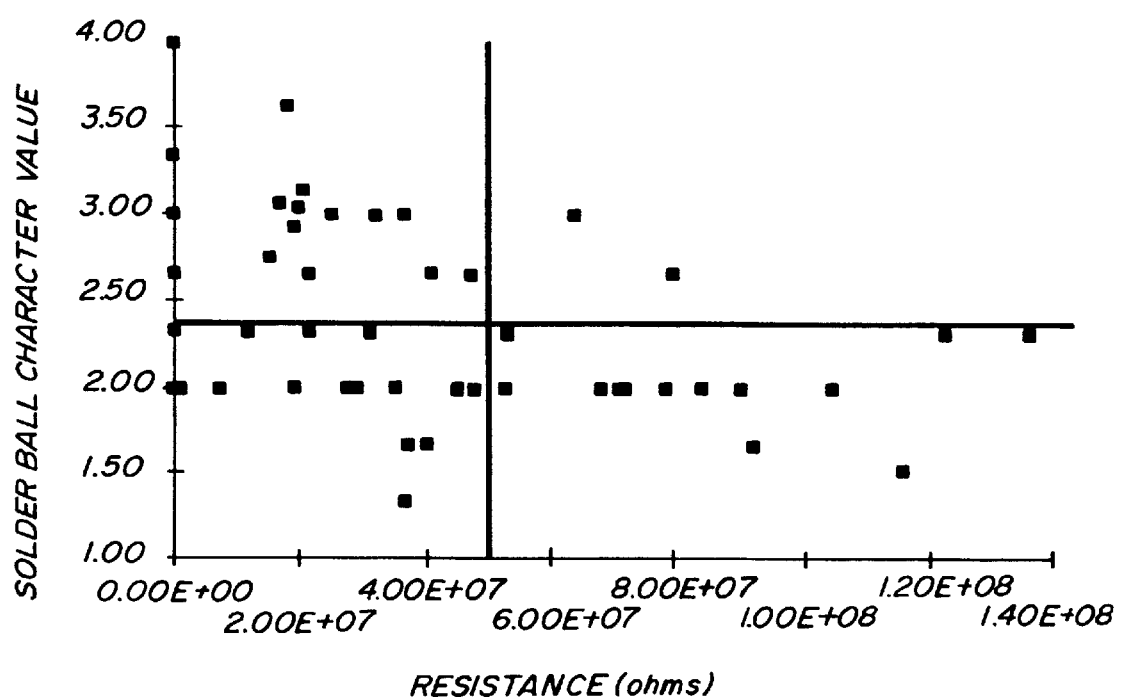
FIG. 14 is a graph showing solder balls versus the resister in the equivalent circuit

The approach of Impedance Spectroscopy is to electrically map physical changes in materials using electrical equivalent components. The logic associated with implementing impedance spectroscopy (IS) for solder paste materials is provided in FIG. 13. The first step in implementing IS techniques for controlling solder paste is to design a solder paste/residue probing system. The probing system implemented has a great effect on the physical phenomenon measured with the solder paste. As an example, a four probe measurement scheme concentrates on measuring the bulk behavior of the material, a 3 probe system measures interface behavior (I.E., reaction, diffusion, adsorption, etc.), and a 2 probe measurements incorporate both interface and bulk behavior. The next step is to design an experiment that will cause changes in the solder paste material that resembles the type of changes that can be seen in manufacturing. After the experiment is designed, the next step is to establish theories and models that map the behavior of the solder paste and to develop an equivalent electrical circuit that maps the same behavior. Once the appropriate equivalent electrical circuit is found, curve fitting routines are employed to derived specific component values within the electrical circuit. From this point on, the characteristic changes in the solder paste can be correlated with specific components or sets of components within the equivalent circuit.

Moisture Absorption and Its Effect on Manufacturing Yields

Figure 15A:
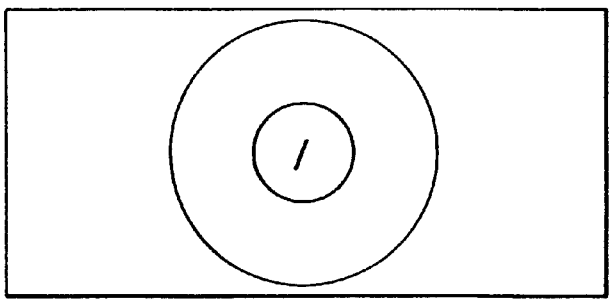
FIG. 15A–D shows solder balling characteristics on a scale from 1 to 4
Figure 15B:
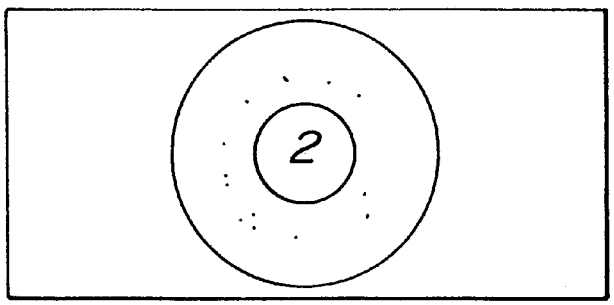
Figure 15C:
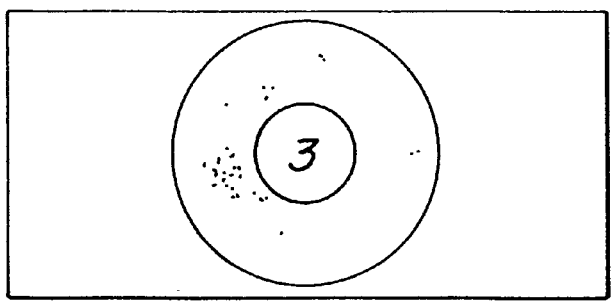
Figure 15D:
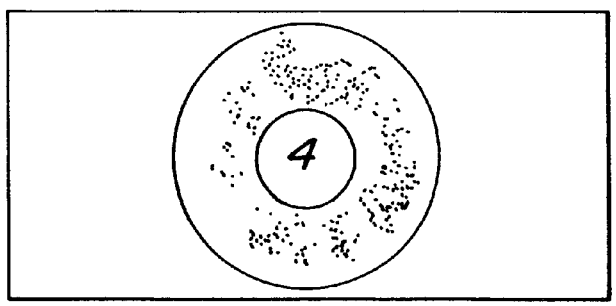

One of the manufacturing anomalies associated with solder paste is moisture absorption from the surrounding environment. Absorbed moisture can cause two changes within the solder paste 1) excessive powder oxidation due to the moisture acting as a catalyst for accelerated oxidation and 2) solder balling due to volatilization of the water vapor during the reflow process. A number of publications by Marquette University (M. Polcyznski, M. A. Seitz, and R. Hirthe, A New Technique for Monitoring Solder Paste Characteristics Proc. of the 14th Annual Electronics Manufacturing Seminar, Naval Weapons Center, China Lake, Calif. (1990). M. Polcyznski, M. A. Seitz, and R. Hirthe, A New Technique for Monitoring Solder Paste Characteristics Surface Mount Tech. 4, p. 54–60, (1990), M. Polcyznski, M. A. Seitz, and R. Hirthe, Measuring Solder Paste Metal Content Using Alternating Current Electrical Impedance Techniques Proc. 1990 International Symposium on Microelectronics, Chicago, 111., October 15–17, p. 174–182 (1990), M. A. Seitz, and R. Hirthe, Thermal Stability of Metal Oxide Surge Suppression Devices, 1990 EOS/EDS Proceeding, Lake Buena Vista, Fla., September 11–13, P. 187–192, (1990), M. Polcyznski, M. A. Seitz, and R. Hirthe, Microstructural Mechanisms Associated with the Electrical Impedance Characteristics of Solder Paste Flux, Proc. of the 1 5th Annual Electronic Manufacturing Seminar, Naval Weapons Center, China Lake, Calif. (1991), M. Polcyznski, M. A. Seitz, and R. Hirthe, Use of AC Electrical Impedance Techniques for Monitoring Microstructural Changes in Electronic Materials, Proc. of the 1991 International Sym. on Microelectronics, Orlando, Fla., October 21–23, P. 431–435, (1991), M. A. Seitz, and R. W. Hirthe, M. Amin, and M. Polcyznski, Monitoring Solder Paste Properties Using Impedance Spectroscopy, Proc. of the 1992 International Symposium on Microelectronics, San Francisco, Calif., October 19–21, P. 503–509, (1992), M. A. Seitz, and R. Hirthe, M. Amin, and M. Polcyznski, Low Frequency Electrical Behavior of Solder Paste, Proc. of the 16th Annual Electronics Manufacturing Seminar, Naval Weapons Center, China Lake, Calif. (1993), M. A. Seitz, and R. W. Hirthe, M. Amin, AC Electrical Characterization of Solder Paste, Proc. Electrecon 93, Indianapolis, Ind., May 19–21, P.14.1–14.18, (1993)) have shown that the impedance data for solder paste changes based on different exposure times and amount of moisture in air. The present invention was able to link this IS data to solder ball failures in solder paste. In order to substantiate this position, a 2-probe IS experiment was conducted with an Alpha RMA 390 and different humid environments and exposure times. The electrical circuit that was used to model the RMA solder paste in a 2 probe configuration was a simple resistor and capacitor in parallel and the frequency range chosen, among many possible range choices, of the stimulus AC waves were from 5 Hz. to 10 kHz. The resistor, in this case, tracked well with the probability of obtaining solder balls in manufacturing. The results of the experiment can be found in FIG. 15. Where the vertical line through the middle of the graph is the lower control limit for resistance and the horizontal line through the graph shows where less than one out of three solder paste patterns will cluster and thus above this horizontal line is unacceptable solder balling and below this line is acceptable solder balling. The y-axis is the level of solder balling (i.e. the severity of solder balling on a numeric scale) and the x-axis is the value of the parallel resistor. FIG. 15A–D shows a graphic representation of the numeric scale for solder balling. FIGS. 15A–D show solder balling characteristics on a scale from 1 to 4 with 1 being preferred, (FIG. 15A) 2 being acceptable (FIG. 15B), 3 being unacceptable (clusters) (FIG. 15C) and 4 being unacceptable (FIG. 15D).

Figure 16A:
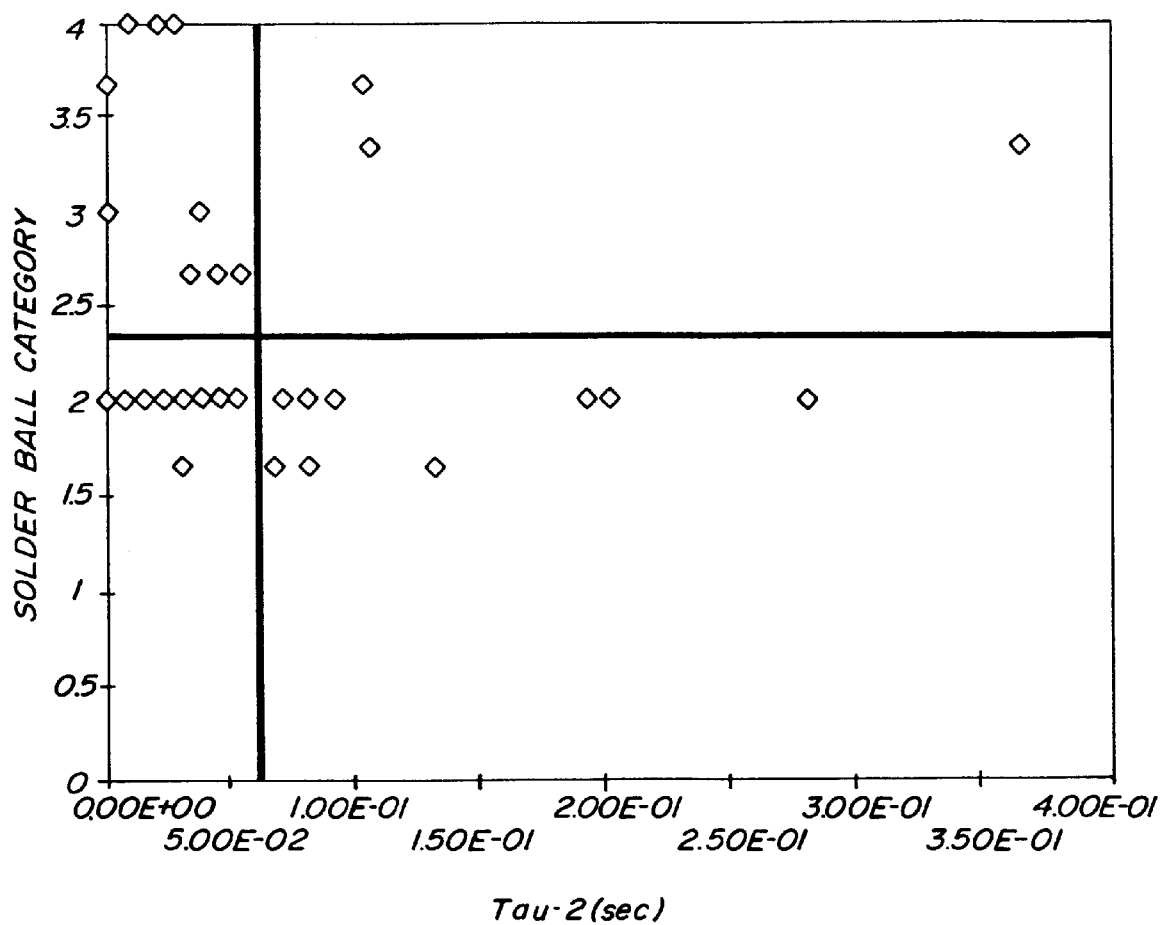
FIG. 16 is a graph showing solder balling versus 4-probe bulk time constant
Figure 16B:
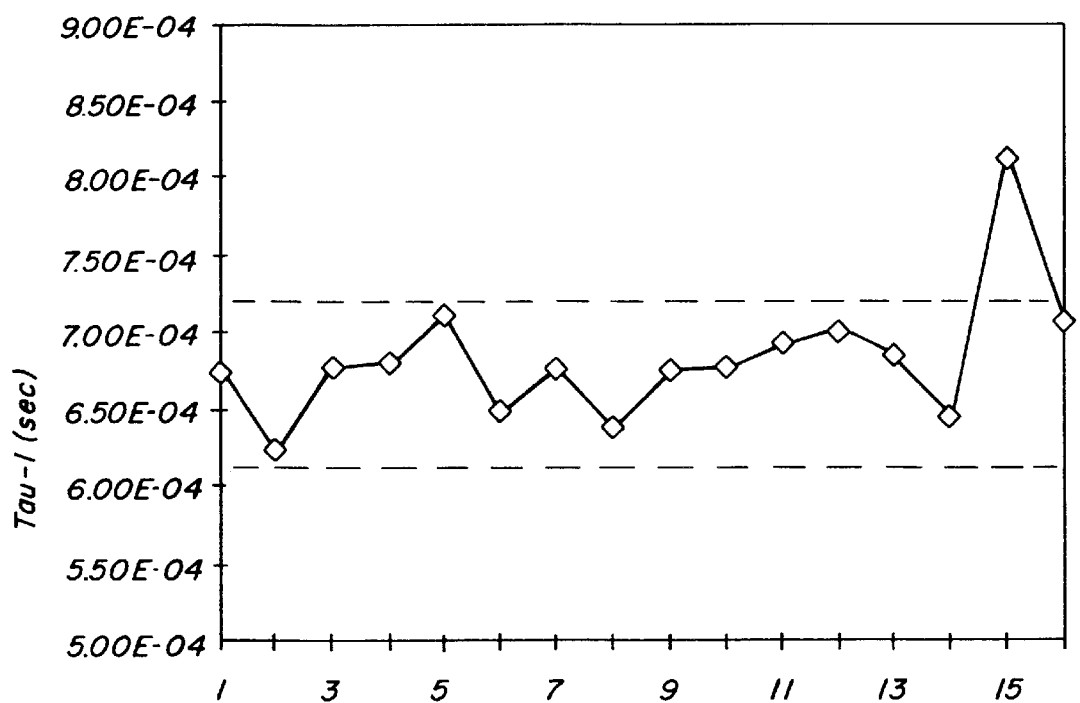
Figure 16C:
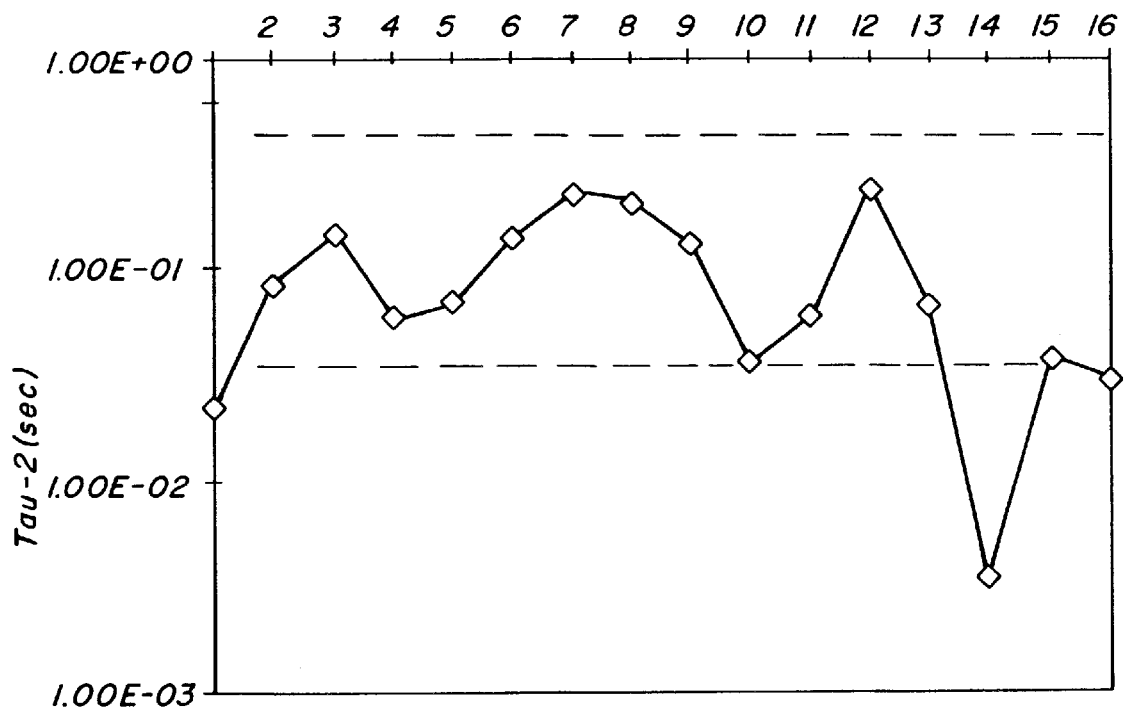
Figure 17:
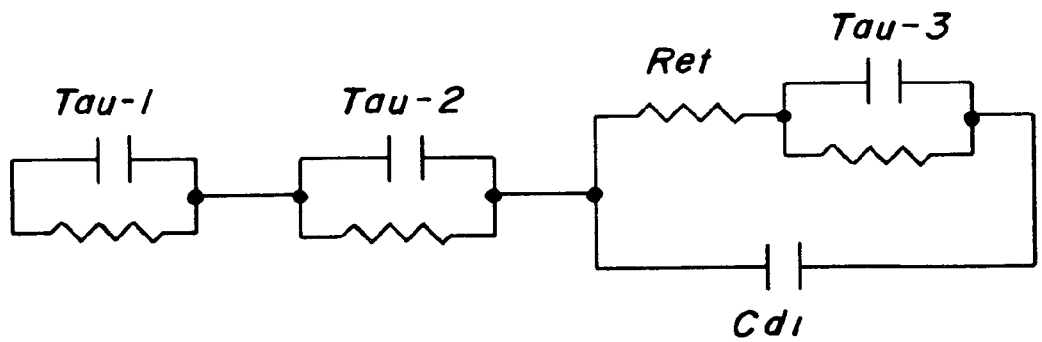
FIG. 17 is an equivalent electrical circuit for AIM 437 water soluble solder paste

Data from the manufacturing floor, in an optimum environment showed that the resistor value stayed between $0.8 \times 10^7$ and $1 \times 10^7$; therefore it can be seen that the lower control limit established on R for this solder paste would be between $5-6 \times 10^7$ in order to avoid solder balling. Moisture absorption can also be mapped using 4 probe instrumentation. The results of another short experiment on the same solder paste is shown in FIG. 16A. Some interesting differences between the 2 probe and the 4 probe data is that there was an evolution of another low frequency RC parallel behavior in the 4 probe configuration. The 2 probe data was measuring the high impedance of the flux-probe interface while the 4 probe technique was measuring the impedance of the flux powder interface. FIG. 17 show how the 2 time constants behaved over time and how it correlated with printability characterists (i.e., skips). Upper and lower control limits are then generated to provide control for use of the solder paste. The upper control limit is at approximately 7.25 E-04 and the lower control limit is at approximately 6.20 E-04 with slips beginning to occur at approximately at 10. In FIG. 16C the upper control limit is the top dashed line in the graph and the lower control limit is the lower dashed line in the graph and the point where slips begin to occur is at 13.

Changes in Rheologic Properties

Figure 18:
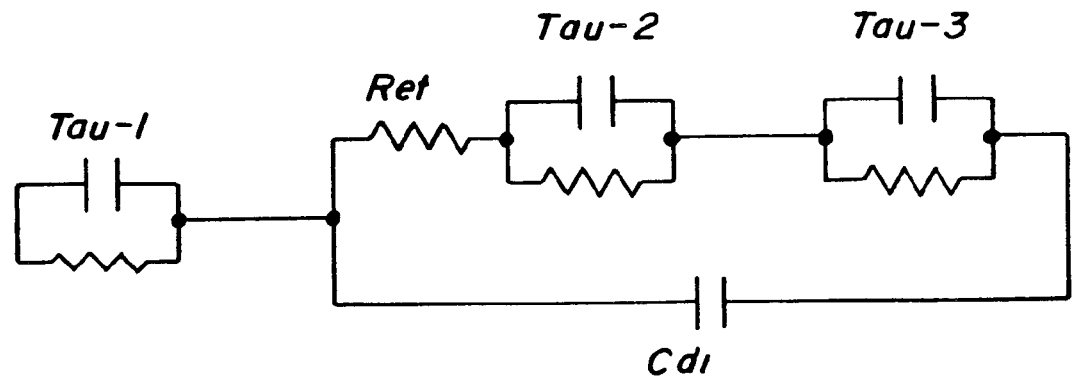
FIG. 18 is and equivalent circuit for Multicore LG02 Water Soluble solder paste

Another property of solder paste that is of interest is the rheologic nature of the solder paste over time. Any changes in the viscosity or thixotropy behavior can have disastrous effects on the ability to print the paste on a circuit card. There are two properties that are traditionally tracked with solder paste: 1) viscosity and 2) thixotropic index. In experiments the rheologic properties were tracked with the IS electrical models. The first paste that was experimented with was an AIM Water Soluble 437 solder paste. The inventors of the present invention were able to map the viscosity change with some of the bulk time constants within the circuit model. The circuit model used for this paste is described in FIG. 18. The circuit model was developed over a frequency range from 5 Hz. to 13 Mhz. (the measurements were made by integrating a higher frequency impedance measuring device.) The ability to track rheologic properties of the solder paste is heavily dependent on the chemistry of the solder paste. With the AIM WS 437 we had a direct linear relationship between the highest frequency time constant and viscosity. Using linear regression techniques, we had a R2 value greater than 0.95! See Table 2 for the fit characteristics for each of the three time constants and viscosity at different shearing rates.

| Immediate Measurement | | | | |
|---|---|---|---|---|
| | High Freq Tau-1 | Mid Freq Tau-2 | Low Freq Tau-3 | Interface Tau-4 |
| Rsq(10)= | 9.92E − 01 | 7.11E − 01 | 3.88E − 01 | 4.57E − 03 |
| Slope(10)= | 1.03E + 10 | 4.60E + 07 | 1.27E + 05 | 2.43E + 05 |
| Rsq(4)= | 9.75E − 01 | 6.75E − 01 | 6.08E − 01 | 1.87E − 02 |
| Slope(4)= | 1.51E + 10 | 6.63E + 07 | 2.35E + 05 | −7.28E + 05 |
| Rsq(0)= | 9.43E − 01 | 6.44E − 01 | 6.83E − 01 | 4.39E − 02 |
| Slope(0)= | 1.83E + 10 | 7.98E + 07 | 3.07E + 05 | −1.38E + 06 |
| Rsq(TR)= | 7.00E − 01 | 4.48E − 01 | 9.10E − 01 | 2.35E − 01 |
| Slope(TR)= | −8.01E + 07 | −3.38E + 05 | −1.80E + 03 | 1.62E + 04 |
| Rsq(10)= | 9.17E − 01 | 2.62E − 01 | 9.62E − 01 | 8.98E − 01 |
| Slope(10)= | 6.08E + 09 | 1.27E + 07 | 5.08E + 05 | 2.09E + 06 |
| Rsq(4)= | 8.71E − 01 | 3.59E − 01 | 9.49E − 01 | 9.71E − 01 |
| Slope(4)= | 1.03E + 10 | 2.59E + 07 | 8.82E + 05 | 3.80E + 06 |
| Rsq(0)= | 8.43E − 01 | 3.85E − 01 | 9.29E − 01 | 9.76E − 01 |
| Slope(0)= | 1.32E + 10 | 3.47E + 07 | 1.13E + 06 | 4.94E + 06 |
| Rsq(TR)= | 7.13E − 01 | 4.51E − 01 | 8.19E − 01 | 9.43E − 01 |
| Slope(TR)= | −7.11E + 07 | −2.20E + 05 | −6.22E + 03 | −2.84E + 04 |
| After 5 Minutes | | | | |

Table 2 R squared values and Slope Values Associated with IS Time Constant Correlations with Solder Paste Viscosity on AIM 437 Solder Paste Experiments were also conducted on a Multicore Water Soluble Solder Paste LG02. One of the characteristics of the LG02 was a presence of a fluorinated activator. The electrical circuit that tracked with the LG02 was a somewhat different from the AIM water soluble in that there was a activator diffusion rate that was significantly from the activator—oxide reaction rate. A graphical representation of the LG02 equivalent electrical circuit can be found in FIG. 18. This circuit established using the same frequency as the AIM 437 described supra. One of the characteristics of the LG02 was the conversion of the $S_n$—Oxide to an O—$S_n$—F compound. This compound. formation had a drastic effect on the thixotropic nature of the solder paste.

Figure 19:
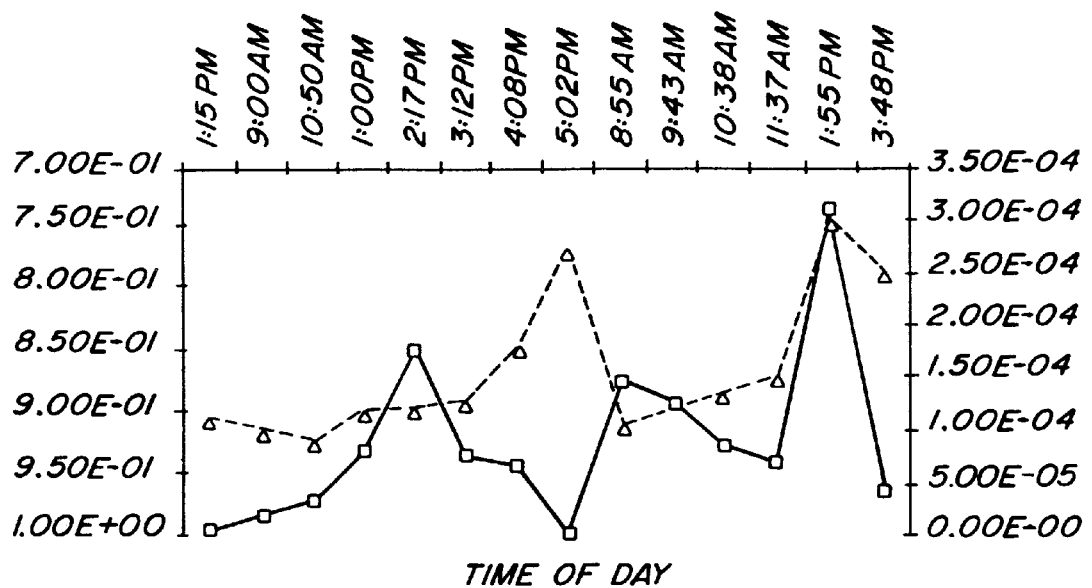
FIG. 19 shows the change made in the Tau-2 (diffusion behavior) mapped along side the change in the thixotropic index. (in a 2-probe measurement)

The inventors believe that the flouridic conversion of the $S_nO$ oxide caused the solder paste material to shear thin more readily under high stress. This shear thinning phenomenon was tracked by an increase in the thixotropic index. In FIG. 19, Tau-2 was tracking this flouridic conversion. Once the O—$S_n$—F formed on the surface of the powder, the thixotropic behavior of the solder paste went through a radical change. It is a well understood phenomenon that the state of the powder surface has a dramatic effect on the rheology character of the solder paste. Using FIG. 21, we would establish a upper control point for tau-2 at around 1×10−4 to ensure a consistent thixotropic behavior in manufacturing.

Increased Powder Oxidation

Figure 20:
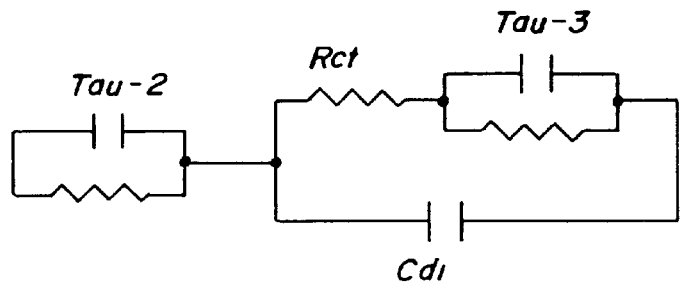
FIG. 20 Equivalent Electrical circuit for mapping oxides in a 0% Multicore RMA Flux FIG. 21 show the surface 4-probe

Experiments were also performed on solder powder to determine the ability of IS measurement techniques to track different characteristics of powder oxidation. Five different powders that have been aged at room temperature conditions from 1 to 5 years were used. The oldest powder was manufactured in 1989 and newest was 1994. The powder was placed in a 0% activator Multicore RMA flux paste and then modeled using the equivalent circuit described in FIG. 20. The Correlation between the age of the powder (i.e. the amount of oxidation) and the IS data is provided in Table 3. This shows that the 4-probe techniques are sensitive to different amounts of powder oxidation.

TABLE 3

Relationship between Powder Oxidation and IS data.

| Date of Powder | Particle Size | Tau-2 |
|---|---|---|
| 1989 | 45 m | 1.7 × 10−3 |
| 1990 | 75 m | 1.2 × 10−3 |
| 1990 | 53 m | 8.2 × 10−4 |
| 1991 | 45 m | 7.8 × 10−4 |
| 1994 | 45 m | 6.9 × 10−4 | d) Probing Hardware

The probes that have been designed to measure solder pastes and residues exist as either of a bulk or surface type. The bulk probes are designed to minimize the environment as a factor when making the IS measurements while the surface probes allow the environment to interact with the solder paste.

Figure 21:
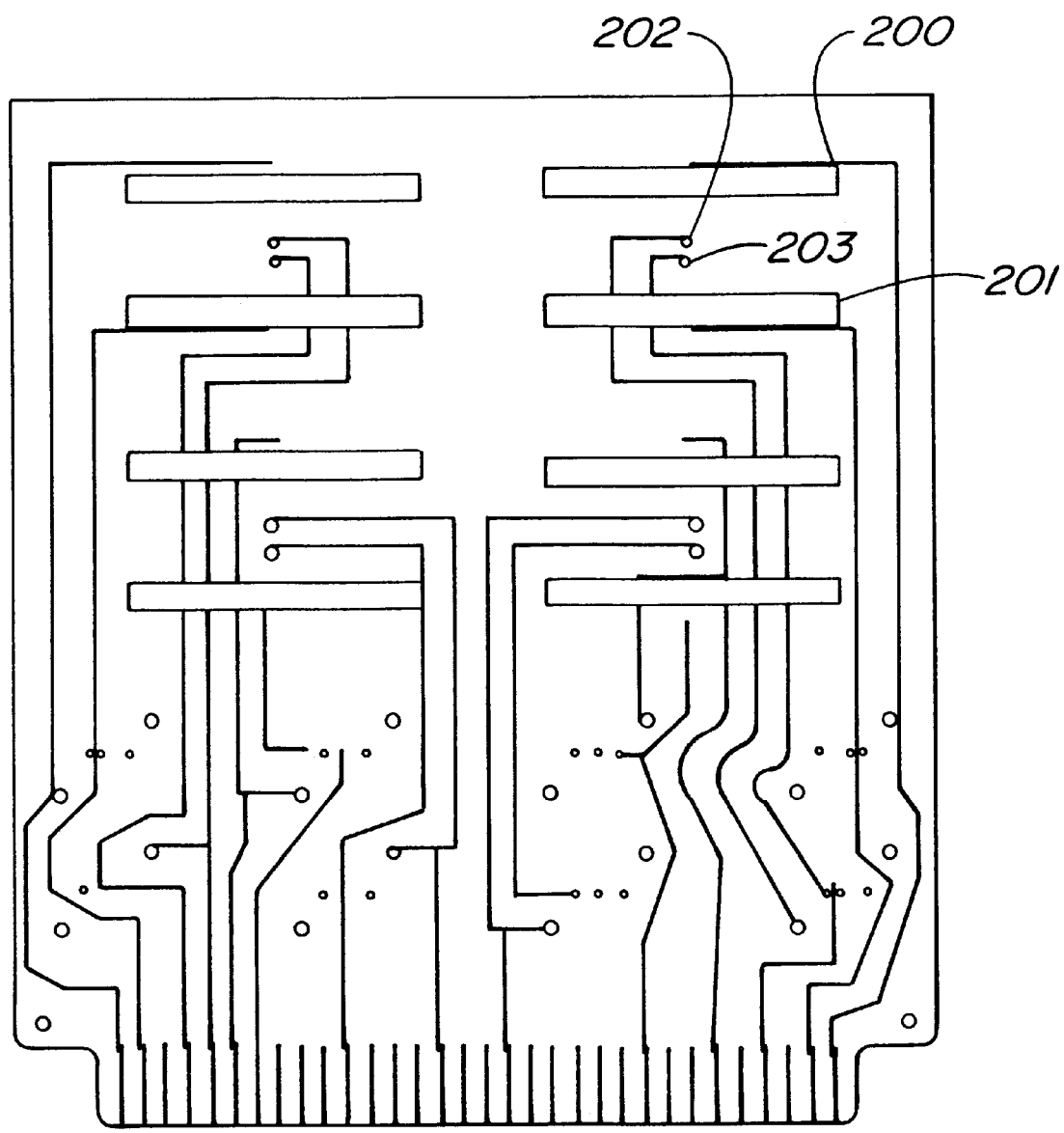

FIG. 21 illustrates the surface 4 probe of the present invention. The surface probe seen in FIG. 21 is designed to have large symmetric current plates and small voltage probes. The small voltage probes are used to avoid disturbing the electric field. The spacing between the voltage probes is also very important in that, being to narrowly spaced may cause intermittent shorting between the probes and to much space between the probes will not allow for an accurate measurement. A spacing of 0.040" was found to work for solder paste being tested. This surface probe was designed to be placed under a screen printer. Spacings less than 0.020" experienced intermittent shorting problems. In FIG. 21 4 surface probes are shown, probe has two large rectangular areas, 200, 201 that are the current plates of the probe, and two small inner circular areas 202, 203 that form the voltage probes of the probe. The current plates can vary between a width of between 0.10 of an inch to 0.50 of an inch and the length can be just about any reasonable length greater than 0.375 of an inch. The diameter of the circular areas can vary from 0.02 to 0.06 of an inch with the optimum being 0.035. The spacing between each voltage probe 202, 203 and the current probes 200, 201 must be greater than 0.02 of an inch and the spacing between each voltage probe must also be greater than 0.02 of an inch.

Figure 22:
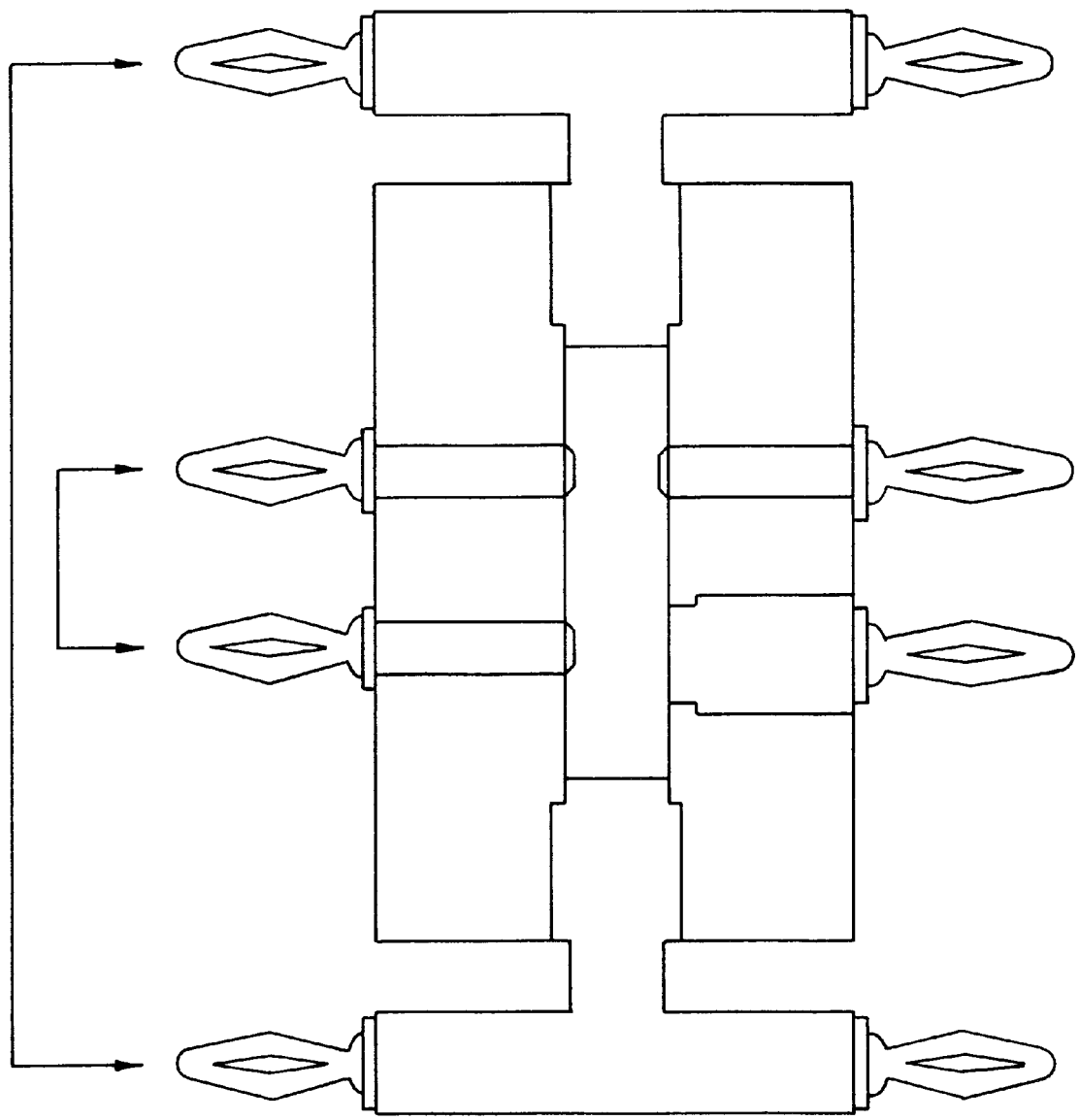
FIG. 22 shows the ¾-pole bulk probe

FIGS. 22 and 23 show the bulk ¾-pole bulk probe. This bulk is designed to minimize the environment as a factor when making the IS measurements. As is the case with the surface probe, the spacing of the electrodes is important for the bulk probes. (See FIGS. 24 and 25 for a complete listing of spacing.)

In the three probe measurement technique, the measured current is that which flows from the working electrode to the counter electrode, while the potential is measured between the reference electrode and the counter electrode.

In the four probe measurement technique, the outer current electrodes are separated from the voltage measuring electrodes. Impedances are calculated using the current flowing through the specimen, and the voltage across the set of inner voltage probes. Since the voltage measuring electrodes do not draw current and are placed inside the current supplying electrodes, electrode impedances are excluded from the impedance measurement. Thus, the electrical behavior of the bulk of the specimen can be extracted from samples that have significant electrode impedances.

What is claimed is:

1. An interface board that enables a lock in amp to perform a user selected 2 or a 3 or a 4 probe impedance spectroscopy measurement, comprising:

a digital computer generating control signals to set up the lock in amp for a user selected 2 or 3 or 4 probe impedance spectroscopy measurement, and generating relay and resistor set up control signals for the programmable load cell;

a digital computer interface, connected to said computer and receiving said control signals from said computer;

an instrument and probe interface connected to said computer interface and connected to the lock in amp and connected to the 2 or the 3 or the 4 impedance spectroscopy probe, and receiving said control signals to set up the lock in amp for a user selected 2 or 3 or 4 probe impedance. spectroscopy measurement;

a power supply;

a relay switching and driver circuitry connected to said power supply and connected to said computer interface;

a programmable load cell having relays that connect resistors in and out the interface board operation of the lock in amp, and said programmable load cell is connected to said instrument and probe interface and to said relay switching and driver circuitry, said relay switching and driver circuitry provides current for the said relays and resistors and the computer interface provides the control signals to programmable load cell to set up the relays and resistors for a user selected 2 or 3 or 4 probe impedance spectroscopy measurement.

* * * * *